(12) United States Patent
Karp et al.

(10) Patent No.: US 6,475,719 B1
(45) Date of Patent: Nov. 5, 2002

(54) DETERMINATION OF FACTORS AFFECTING GENE REGULATION AND/OR GENE REPLICATION

(75) Inventors: Matti Karp; Matti Korpela, both of Turku (FI)

(73) Assignee: Bio-Orbit Oy, Turku (FI)

( * ) Notice: Subject to any disclaimer, the term of this patent is extended or adjusted under 35 U.S.C. 154(b) by 0 days.

(21) Appl. No.: 07/768,741

(22) PCT Filed: Apr. 20, 1990

(86) PCT No.: PCT/FI90/00112
§ 371 (c)(1),
(2), (4) Date: Oct. 21, 1991

(87) PCT Pub. No.: WO90/12887
PCT Pub. Date: Nov. 1, 1990

(30) Foreign Application Priority Data

Apr. 20, 1989 (FI) .................................................. 891899

(51) Int. Cl.[7] ............................. C12Q 1/68; C12N 1/21; C12N 15/63
(52) U.S. Cl. ........................ 435/6; 435/69.1; 435/320.1; 435/252.3; 435/252.33; 435/455; 435/7.1; 435/29; 435/325; 435/235.31; 435/254.1; 536/23.1; 536/23.5; 536/24.1
(58) Field of Search ........................ 435/6, 69.1, 172.1, 435/320.1, 252.31, 252.33, 455, 7.1, 29, 325, 252.3, 254.1, 5; 536/23.1, 23.5, 23.2, 24.1, 27; 935/27, 29

(56) References Cited

U.S. PATENT DOCUMENTS 4,806,471 A    2/1989   Molin et al.

FOREIGN PATENT DOCUMENTS

EP   0 121 386   10/1984
SE   424090      6/1982

OTHER PUBLICATIONS

Danbara et al. PNAS (USA) vol. 78, No. 8, pp. 4699–4703, Aug. 1981.*

Ptashne Nature vol. 322 pp. 697–701, Aug. 1986.*

Watson et al. "Recombinant DNA: A Short Course" 1983 W. H. Freeman and Co., New York, N.Y. pp. 86–87.*

\* cited by examiner

*Primary Examiner*—David Guzo
(74) *Attorney, Agent, or Firm*—Banner & Witcoff, Ltd.

(57) ABSTRACT

The invention relates to a method for determining a factor affecting a cell, which affects directly or indirectly the DNA, RNA and/or proteins of the cell or their synthesis machinery, in which recombinant DNA plasmid is transferred into the cell, and the initial point or points of the reproducing machinery responsible for its replication are subject to an adjustable promoter, which is controllable either by positive or negative feedback; the cell containing the recombinant DNA plasmid is brought into contact with the affecting factor; the affecting factor is allowed to affect the cell containing the recombinant DNA plasmid for a suitable time, after which the promoter adjusting the starting point of the reproducing machinery responsible for the replication of the recombinant DNA plasmid starts growing in the cell, unless the affecting factor has not inhibited the replication of the plasmid; the shift of the copy number of the recombinant DNA plasmid in the cell is determined directly or indirectly.

28 Claims, 30 Drawing Sheets pCSS302

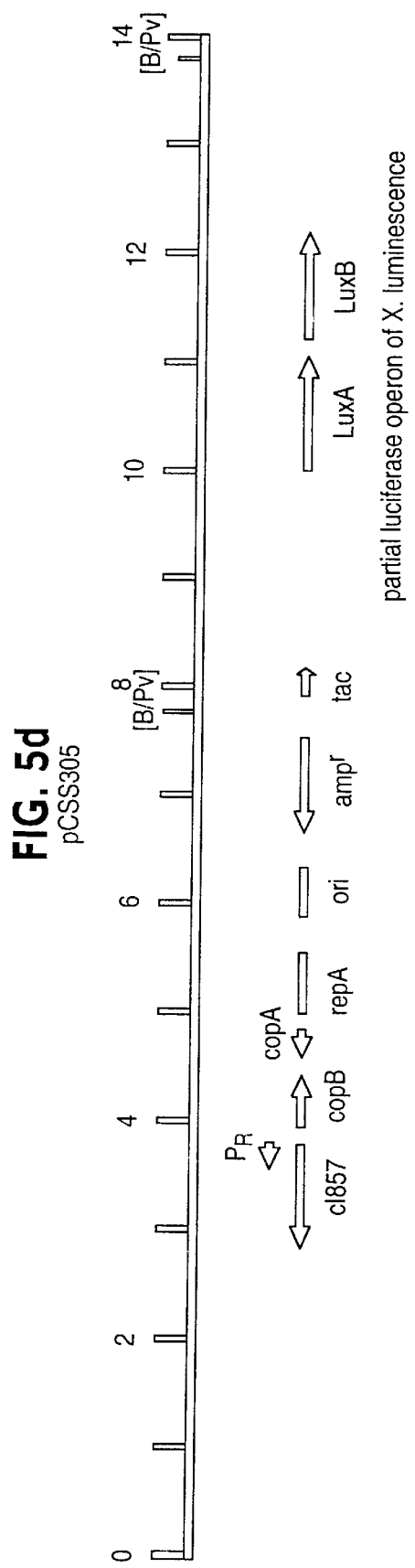

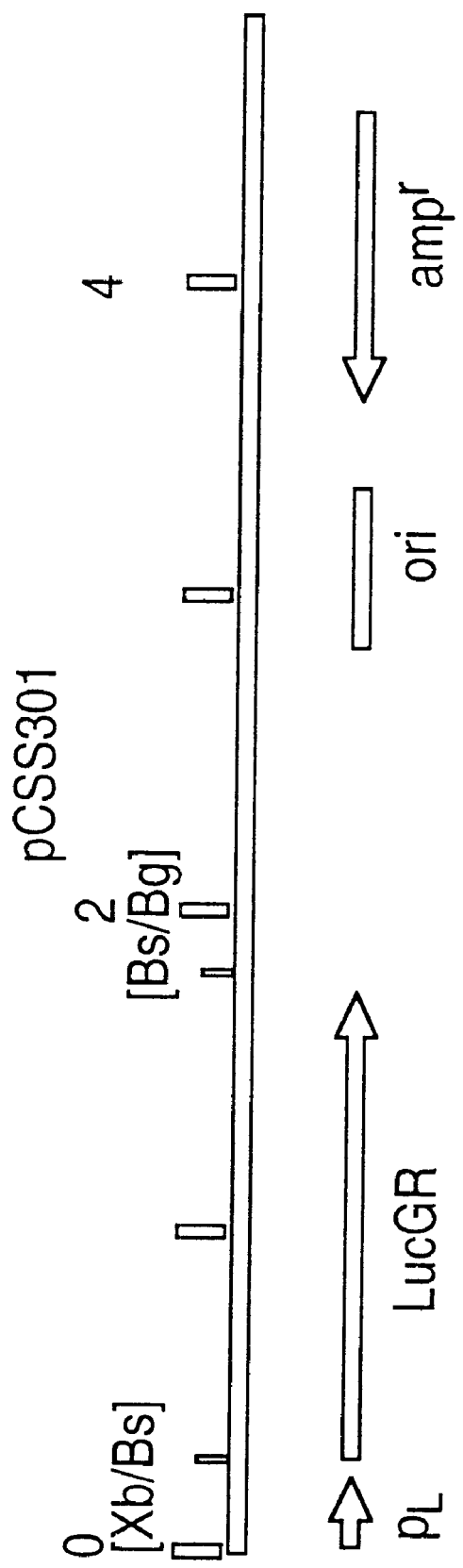

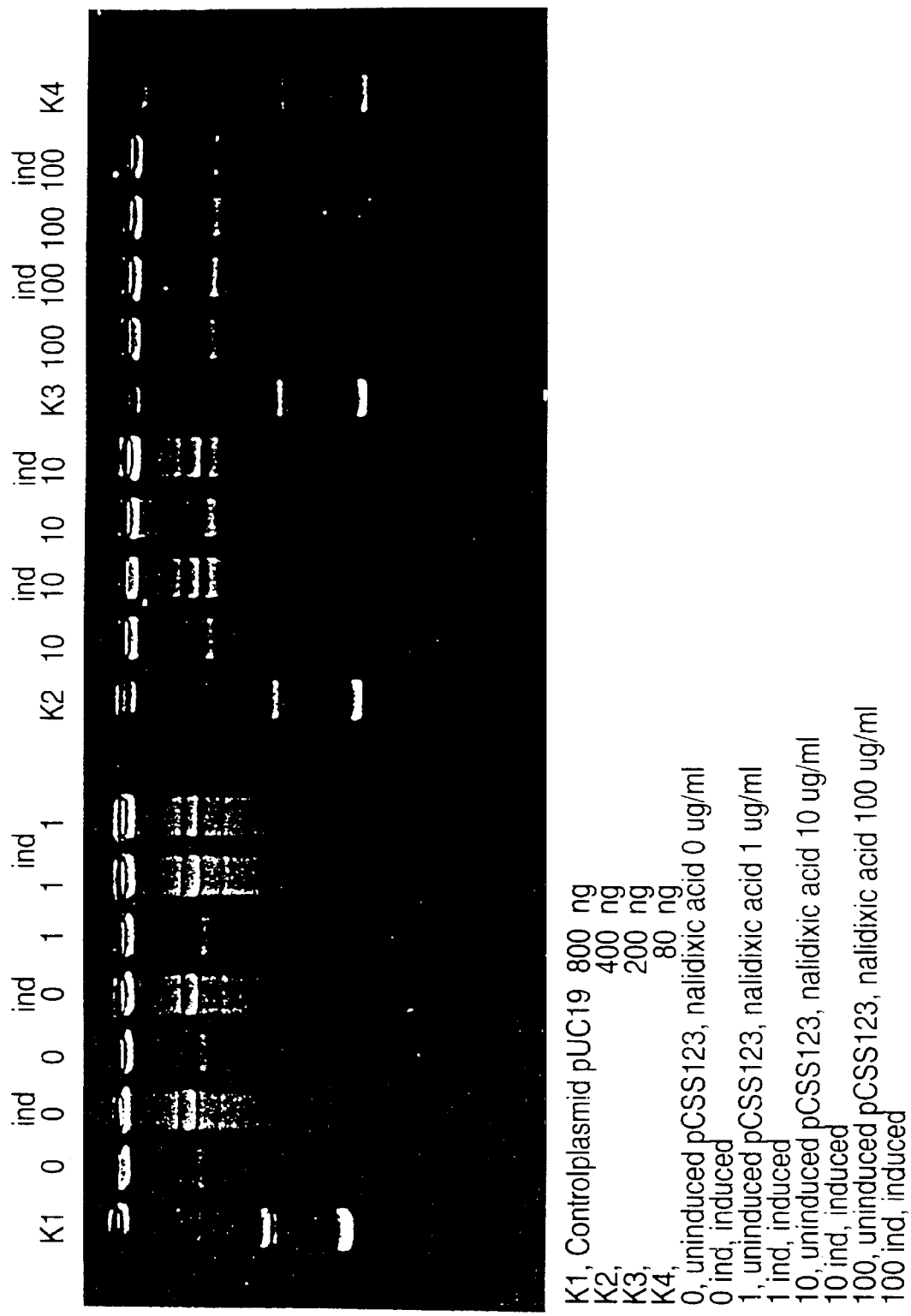

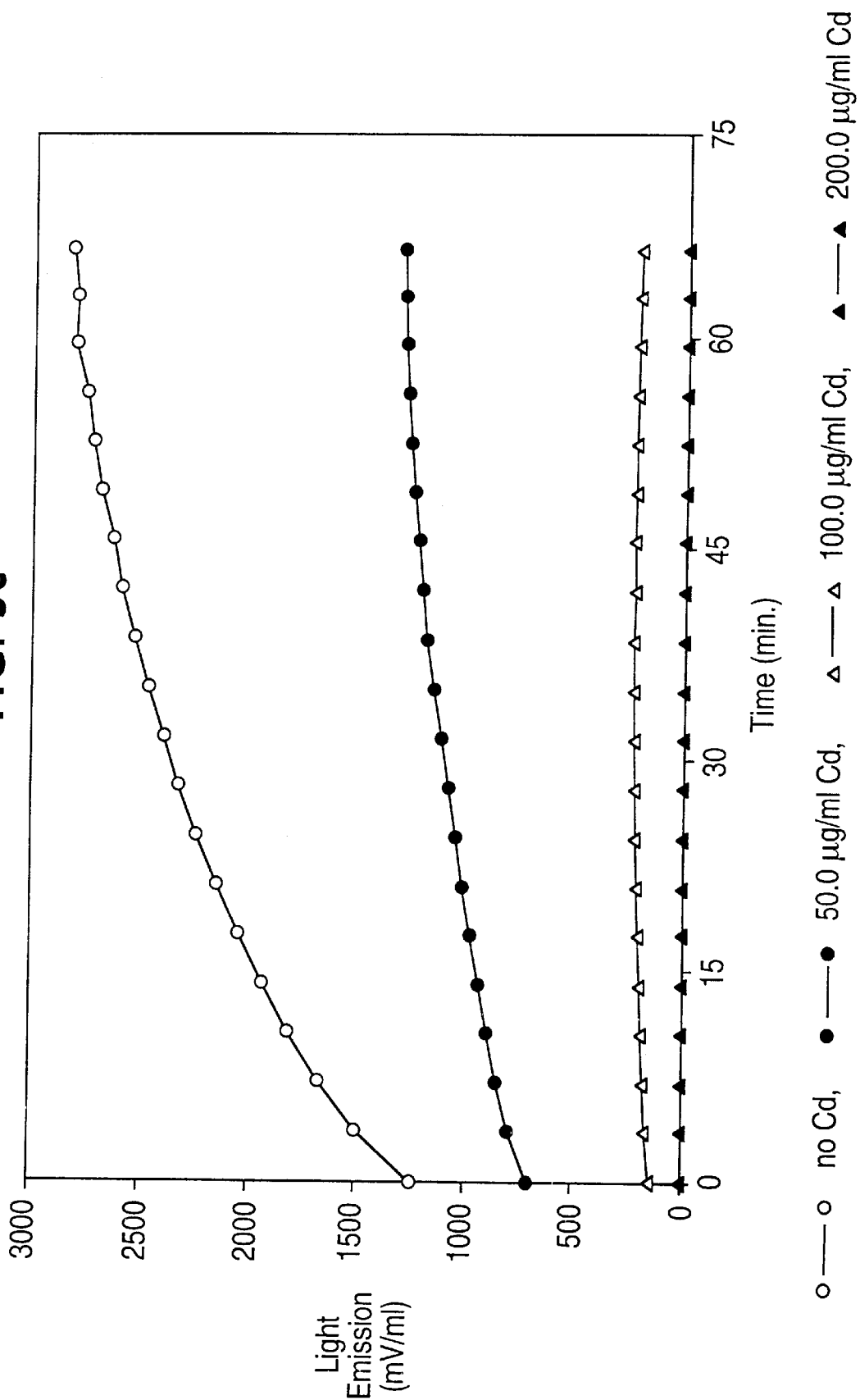

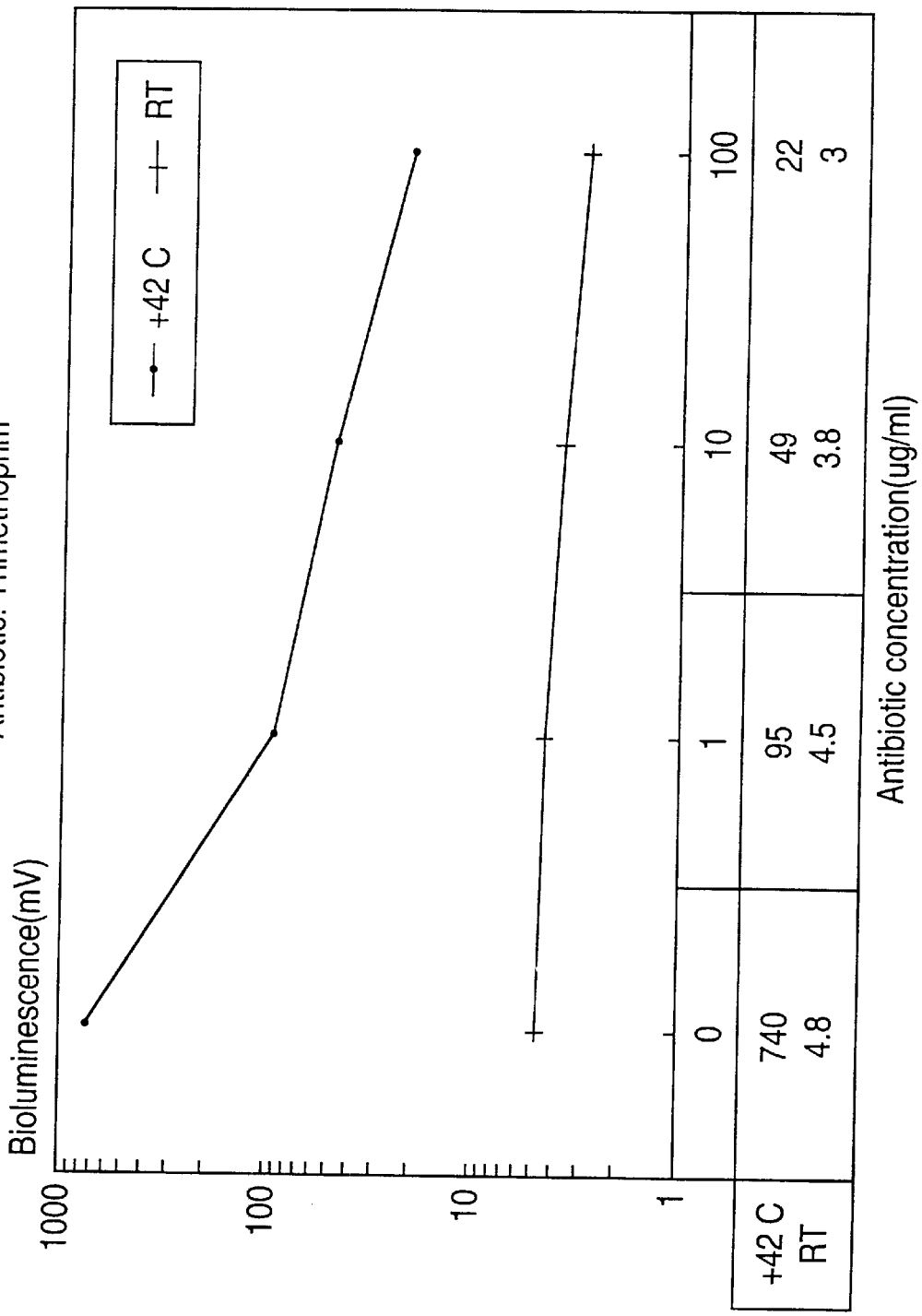

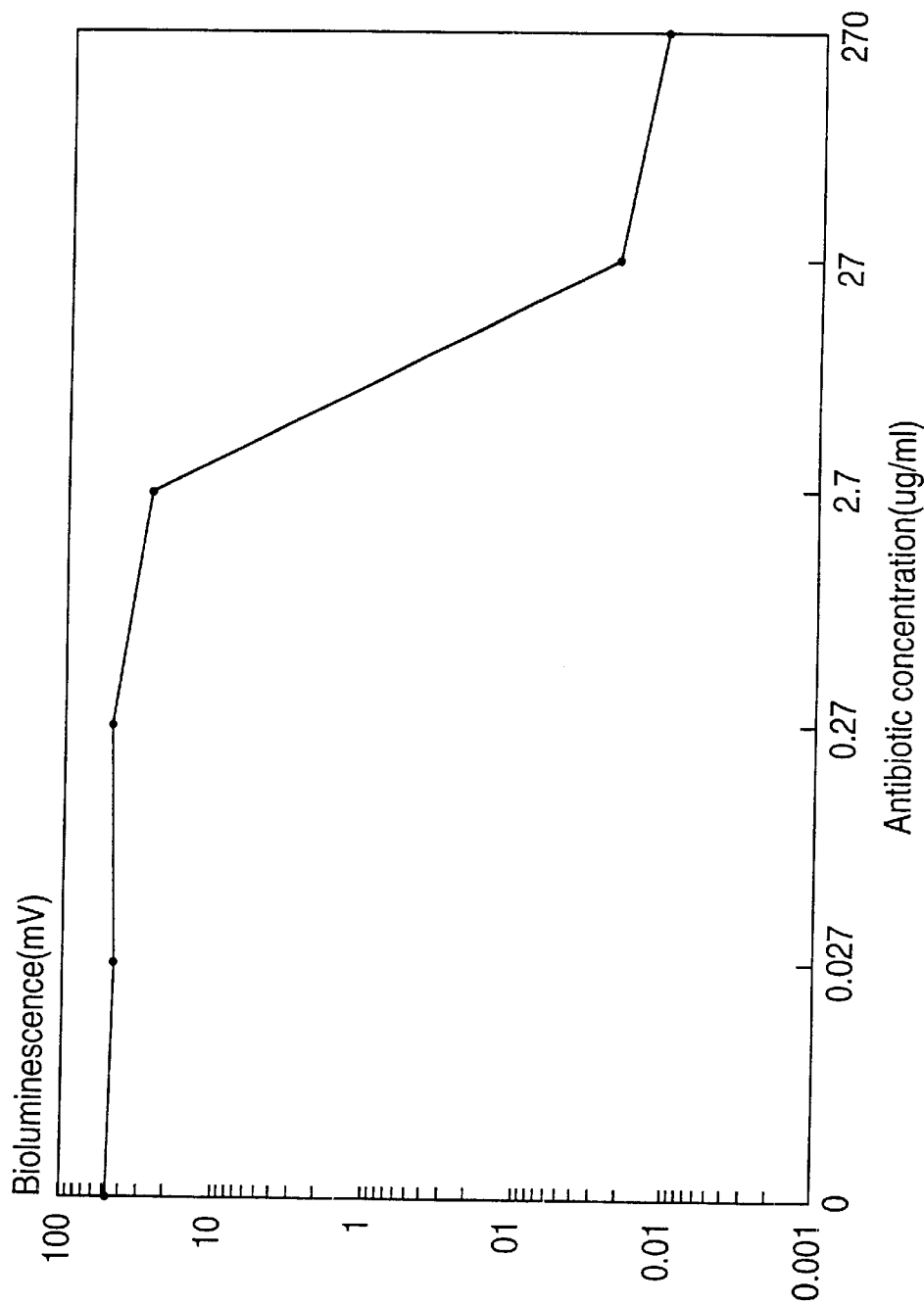

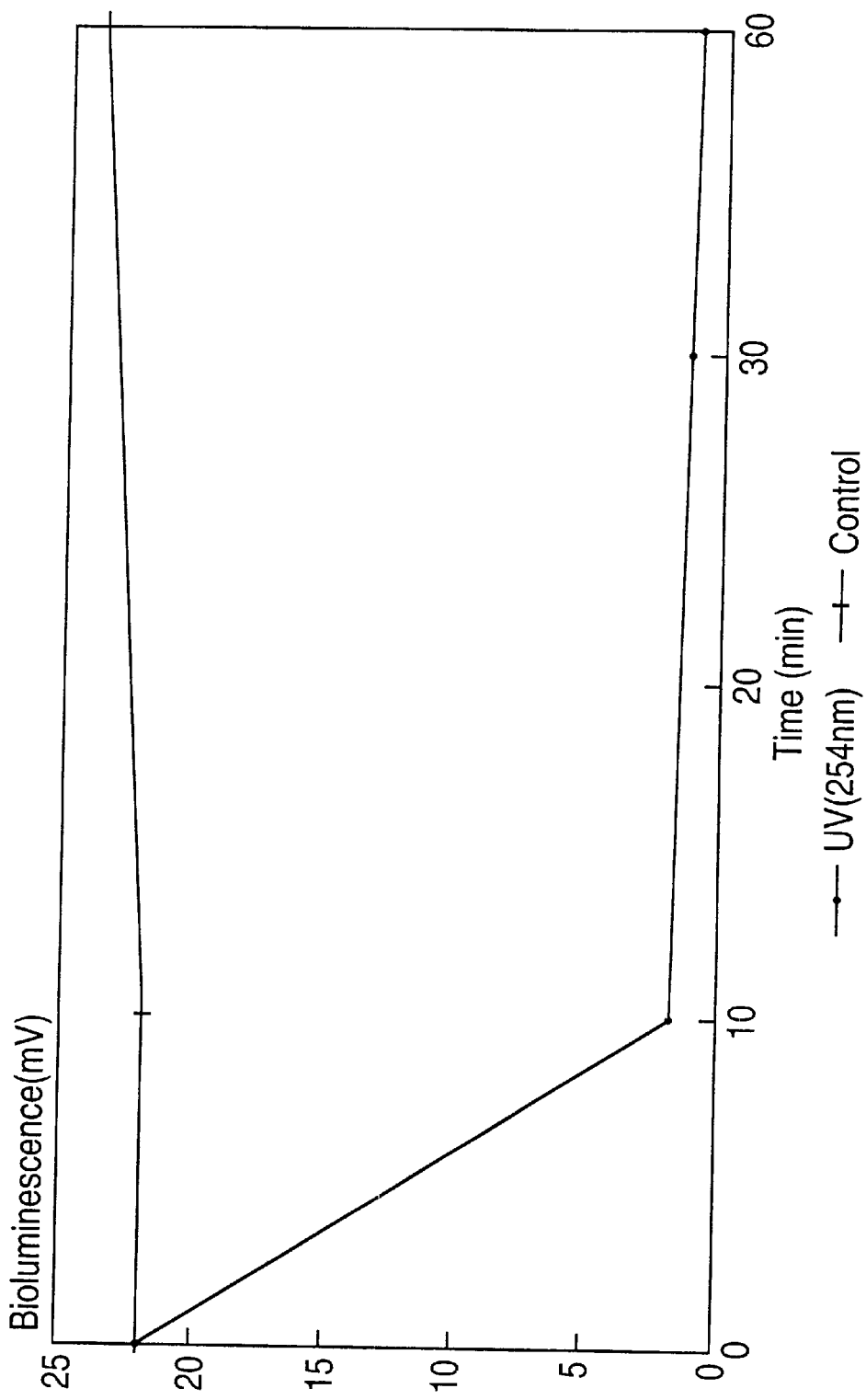

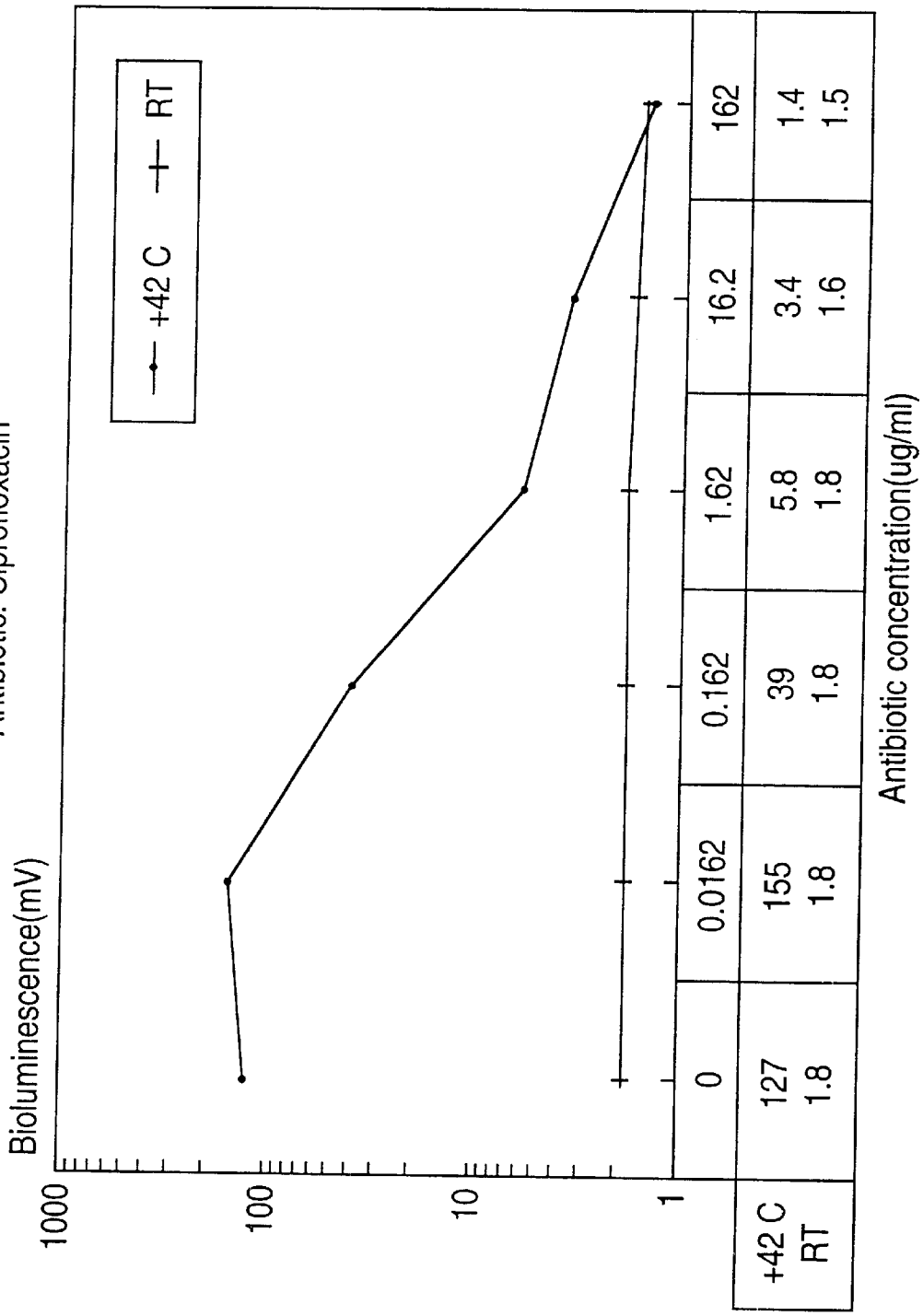

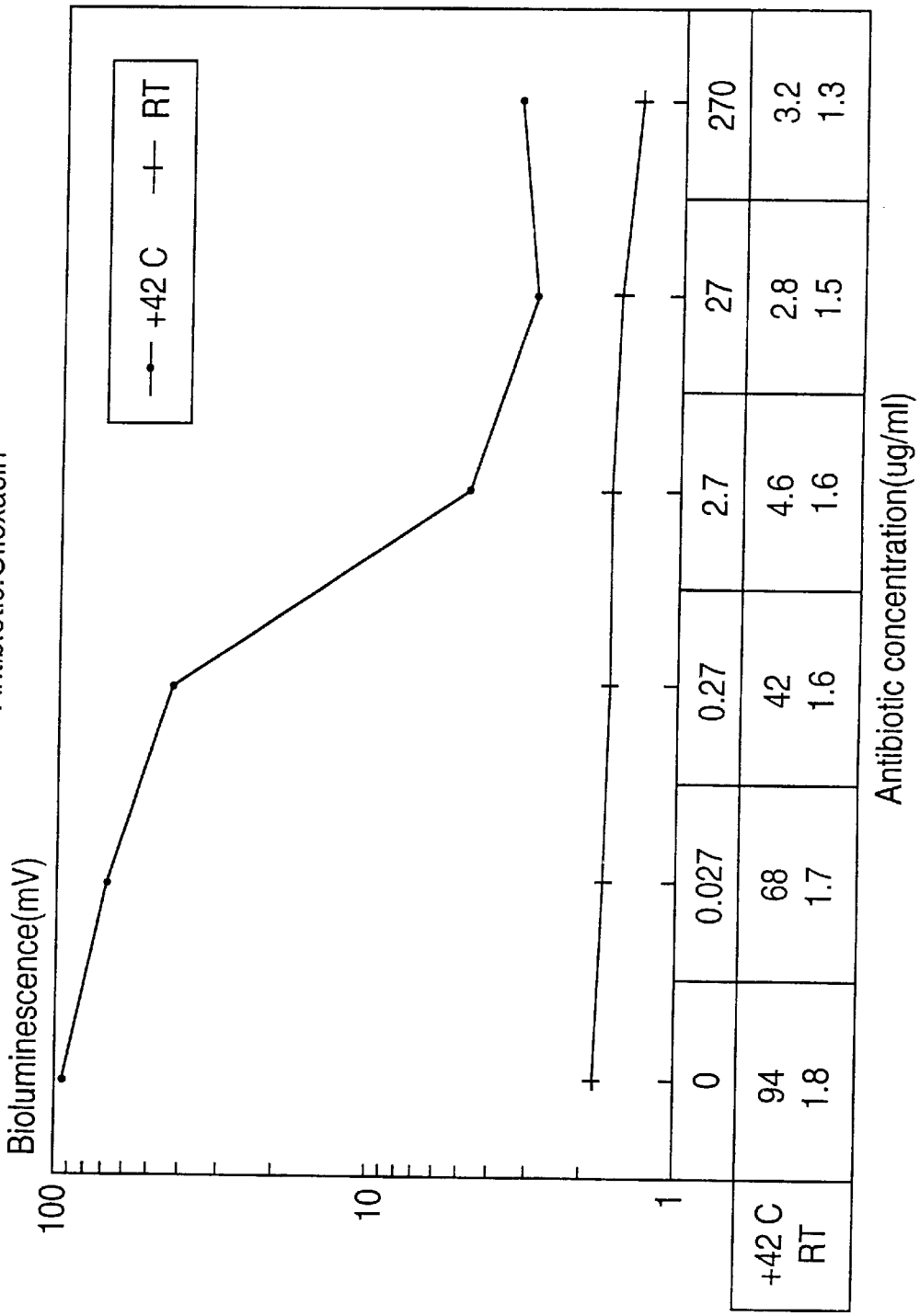

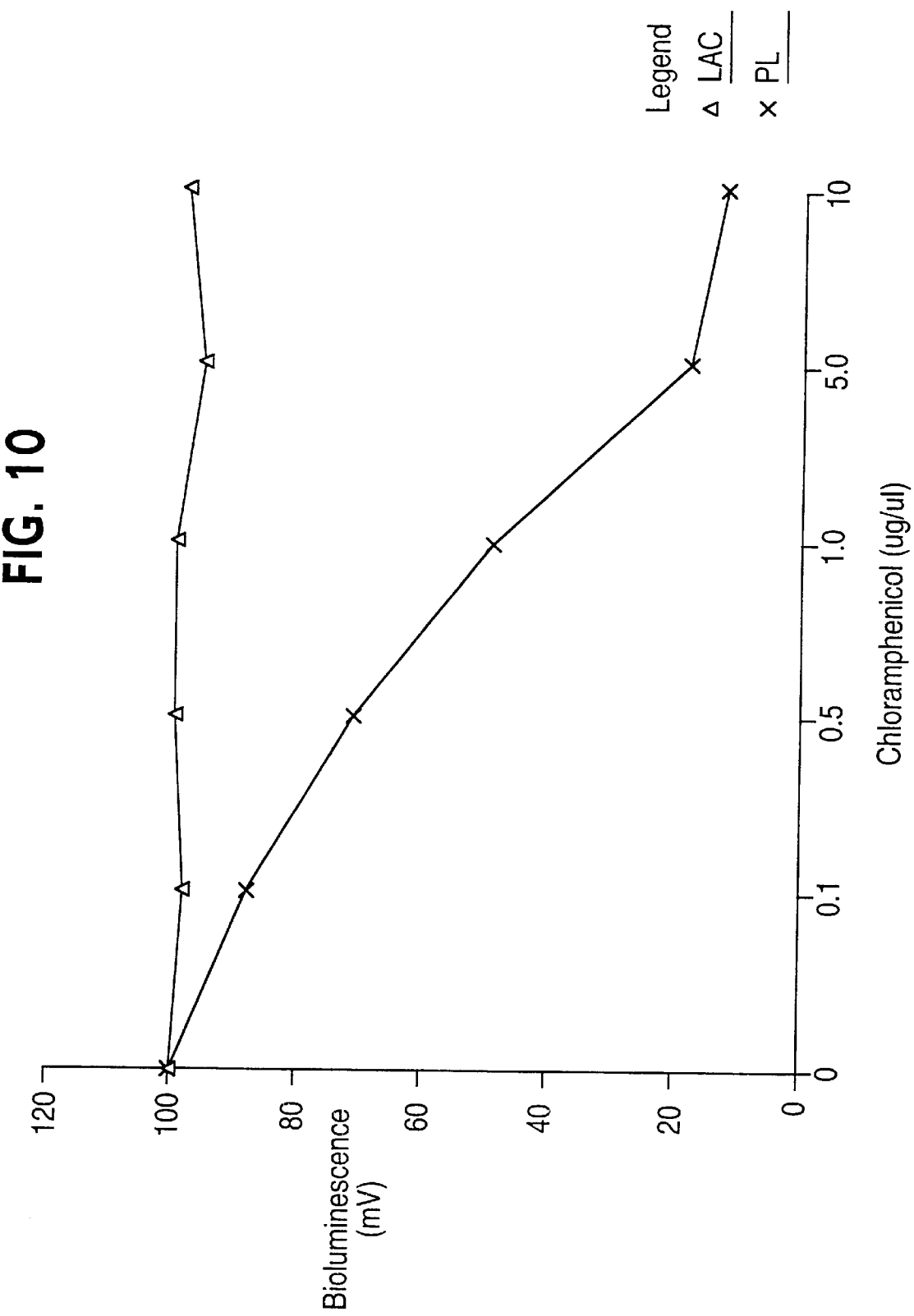

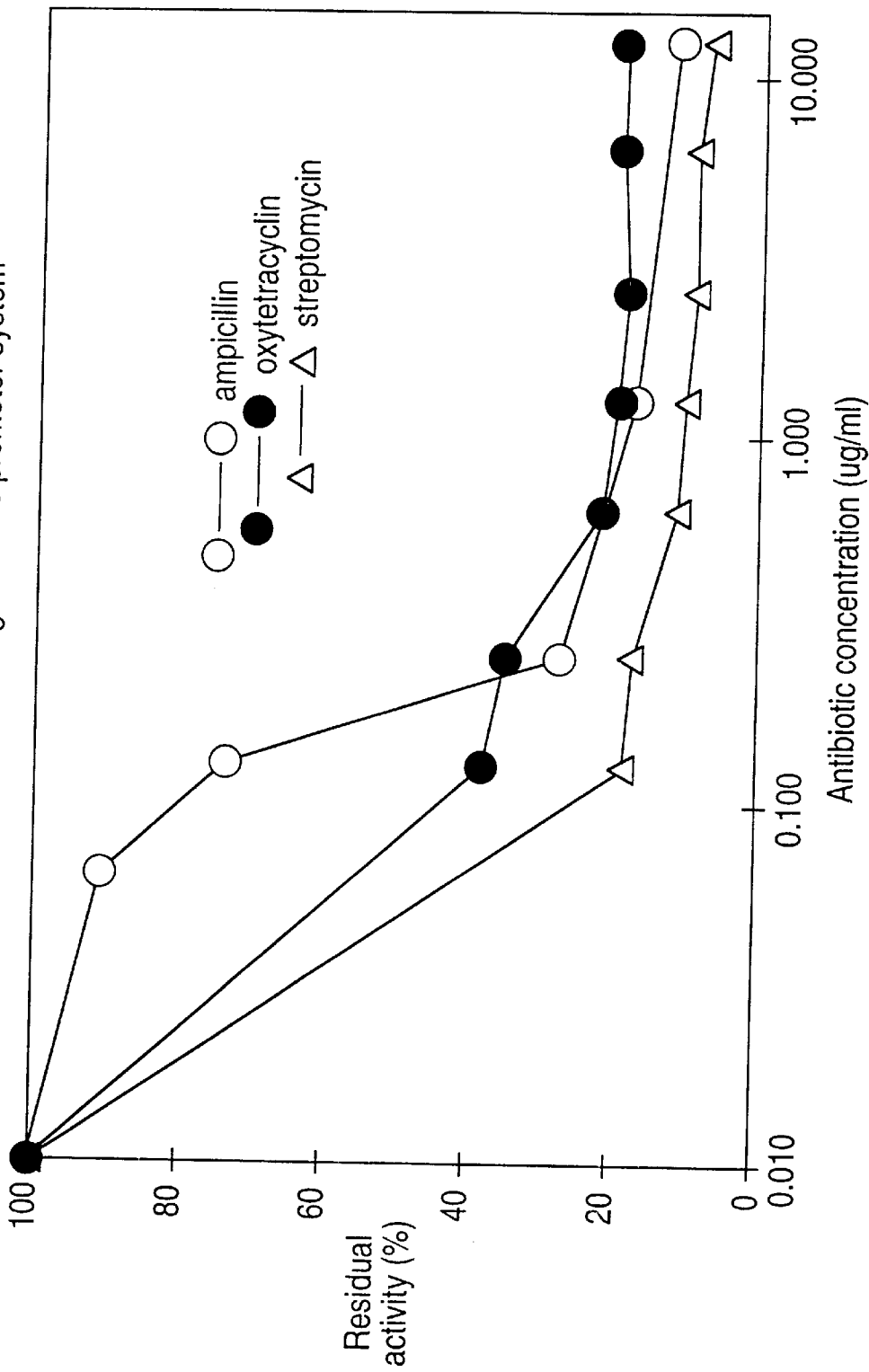

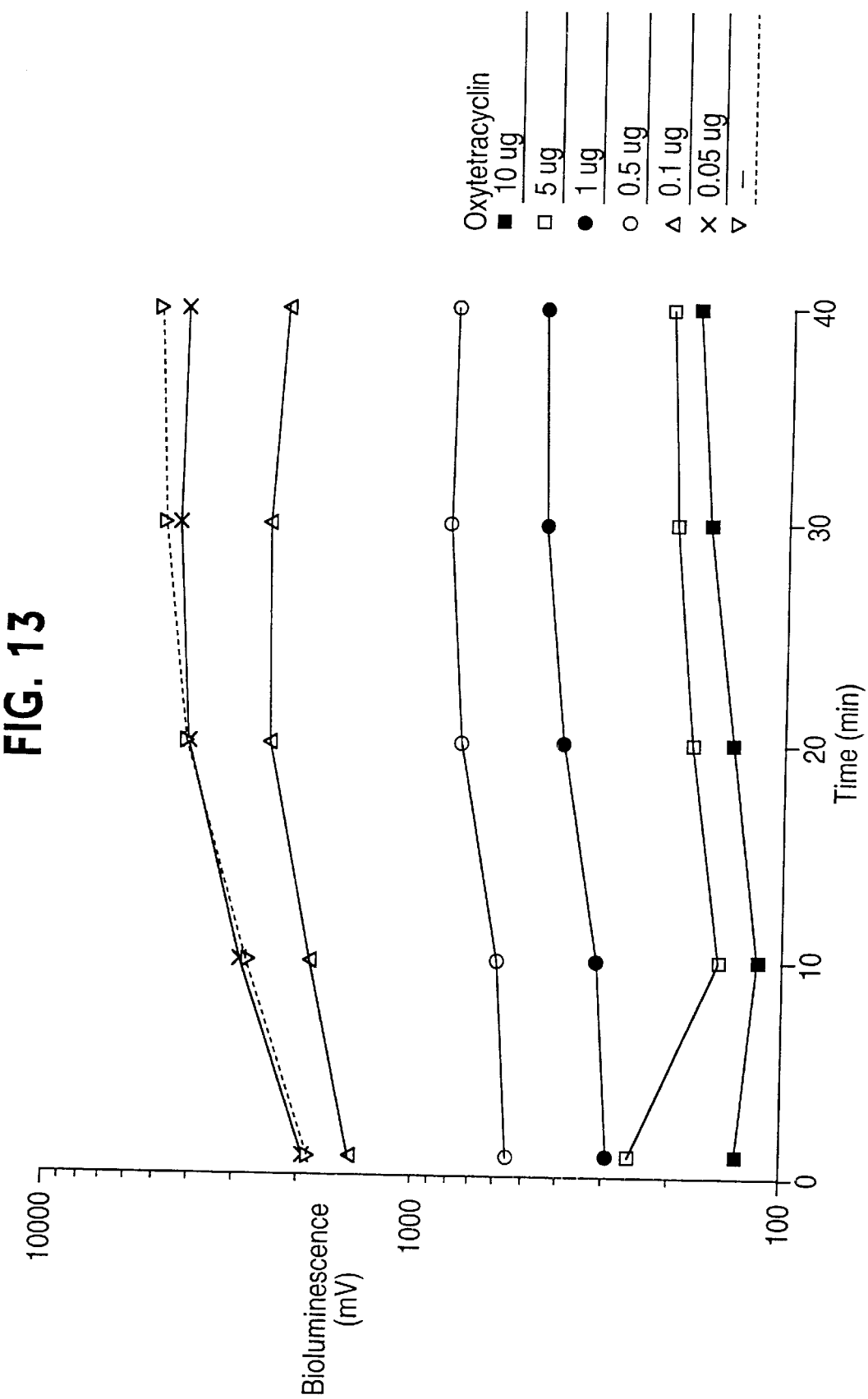

Testing antibiotics with lucGR under pL-promoter

Glucose titration

DETERMINATION OF FACTORS AFFECTING GENE REGULATION AND/OR GENE REPLICATION

Biotests are methods where one uses living cells or organisms as tools to detect different analytes. Many of those methods utilize bacterial or yeast cells. Procaryotic organisms and especially *Escherichia coli* bacterium are very well characterized. Yeast cells are eucaryotic organisms and grow as single cells. The cultivation of yeast is easier than the cultivation of higher eucaryotes. Yeast cells grow in simple cultivation media and they do not need addition of complicated growth factors. The knowledge of yeast is expanding rapidly and comprehensive maps of genes are known. Hundreds of specific mutations for both bacteria and yeast are known. With knowledge of specific mutations it is possible to study the activity of specific reactions and metabolic pathways. For instance with antibiotic sensitive bacterial mutants trace amounts of antibiotics cause changes in the metabolism or in the membranes. Using antibiotic sensitive bacterial mutants, one is able to develop very sensitive tests to measure residual antibiotics from biological material. Bacteria and yeast with mutations in their DNA repair mechanisms, or mutants whose cell membranes might be porous for different small molecular weight substances, e.g., antibiotics, are more sensitive to genotoxic substances than wild type. Using different mutant strains, one is able to measure for the presence of antibiotics and toxic or mutagenic agents. Genetic engineering techniques can be used to transfer new characteristics into bacteria or yeast cells. The new characteristics can be provided by proteins which are encoded by viruses. The protein do not exist naturally in the target organism. Use of genetic engineering techniques expands the applicability of bacteria and yeast cells for use in biotests.

The universal genetic code of DNA is similar in each organism. The relationship between carcinogenicity and mutagenicity is the basis for using tests for mutagenic agents as prescreening tests for carcinogenic agents. Testing for carcinogenicity in animals is extremely expensive and time consuming. Use of tests for mutagenic agents as a quick screening method for carcinogenicity has raised hope and interest. The quick screening method for carcinogenicity would decrease animal-based carcinogenicity testing.

The AMES-test (Ames, B. N., McCann, J. and Yamasaki, E. (1975) Mutat. Res. 31, 347) is the test used most often to screen for mutagenic agents. The AMES-test utilizes *Salmonella typhimurium* as a test organism. Utilizing the AMES-test one is able to detect the genotoxicity of most mycotoxins, aromatic amines and polycyclic hydrocarbons. However, the Ames-test is not able to detect the genotoxicity of carcinogenic metal salts or chlorinated hydrocarbons. The *S. typhimurium* strains used in the AMES-test contain point mutations in the biosynthetic route of the amino acid histidine. As the bacteria are exposed to the action of mutagenic substance, a reversion mutation occurs in the gene for histidine biosynthesis and the bacterium starts to produce histidine endogenously. Endogenous production of histidine gives the cell the ability to grow on minimal growth medium containing no added histidine. A pitfall in the AMES-test is poor sensitivity and slow performance. In the AMES-test all other genotoxic changes such as those acting on enzymes remain undetected. The test is also rather expensive for each particular compound tested.

A test for the detection of genotoxic substances based on bioluminescence is known (Ulizur, S., Weiser, I. and Yannai, S. (1980) Mut. Res., 74, 113–121). In this method, dark mutants of *Photobacterium leioanathi* and *P. fischeri* are used. In the presence of genotoxic substances, these strains start to emit light. The theoretical background of the method remains somewhat obscure. It has been speculated that the effect of removing a repressor or preventing its formation combined with a change in the chromosomal DNA of the bacterium might trigger the formation of light producing proteins. Different genotoxic substances act with different rates in this test due to the variety of different classes of substances. This test is faster than the Ames-test but is by no means easier to use. The bacteria used in the test should produce light during long and varying periods of time (30 min to 10 h) depending on the substance. The bacteria used are not capable of stably emitting light, which makes the method somewhat problematic. Due to these facts, the method is not easily automated for use in routine work when there are a lot of specimens to be analyzed. Additionally, being of marine origin, the cultivation temperature of the bacteria is rather low, 15° C.—it is not known how well the effect of genotoxic substances correlate to the effects on man whose body temperature is 37° C.

Antibiotics, used as medicines against microbial invasion, are detected from body fluids in order to study the dosage and penetration of the medicine. The effective therapeutic range of the antibiotic is often rather narrow and the risks due to overdosage might be large. It is also important to measure the presence/concentration of antibiotics in meat and cow milk due to symptoms in people with allergies to antibiotics. The cow milk used in cheese production should not contain antibiotics due to the fact that cheese making bacteria are not able to grow in antibiotic-contaminated milk. Common methods for detecting antimicrobial medicines are microbiological methods performed on agar. A direct method is to measure the inhibition of the growth of sensitive bacterial strains. One can also measure some metabolic parameters, such as acid production of a sensitive strain of bacteria, using proper color indicators.

Typical examples of agar diffusion tests are cylinder, hole or disk methods. The difference between these tests is in the way the sample is applied to the agar and also in the way the bacteria are utilized in the test.

Since microbiological methods utilize bacteria or their spores, the sensitivity of the test bacteria is of utmost importance. In the tests described above compromises had to be made in the choice of a suitable test strain since great sensitivity against antimicrobial agents and other characteristics needed for the test strain have not been found in the same strain of bacteria.

Major drawbacks when using microbes in antibiotic residue tests are slow speed and insensitive performance. In these methods one controls the growth of a test strain and thus the test cannot be performed in an hour. This is due to the fact that growth of microbes is a slow process even in its fastest mode. In addition, in many cases spores or freeze-dried microbes are used which make the tests even slower to perform.

Antibiotic detection methods based on bioluminescence measurement are known. Ulizur (1986, Methods Enzymol., 133, 275–284) describes three different ways to use bioluminescence for the detection of antimicrobial agents: a) lysis-test, b) induction test and c) bacteriophage test. In the first one, the lux-genes isolated from *Vibrio fischeri* produce luciferase protein which in the presence of substrates produces light. The genes have been cloned into a plasmid and transferred to *Bacillus subtilis*. The *B. subtilis* strain utilized is sensitive to antibiotics which affect bacterial membranes. Examples of such antibiotics are penicillins and cephalosporins. In the lysis-test, the lux-gene-containing *B. subtilis* is grown together with a test sample. If the test sample contains an antibiotic, the synthesis of cell wall components is prevented and the bacteria are lysed. Thus the culture yields lower light emission when compared to a culture lacking the test sample.

The induction test utilizes dim mutants of *P. phosphoreum* bacteria, which do not produce light. The induction test and other bioluminescence tests developed by Ulizur are based on exploitation of the chromosomal DNA of the target cell. Antibiotics affecting protein synthesis are detected in the induction test. When the bacteria are incubated together with compounds that bind to DNA, the bacteria start to produce light, i.e., protein synthesis is initiated. If there is any antibiotic present affecting the protein synthesis then there is a decline in light emission. The amount of antibiotic present is quantitated when compared to a blank without antibiotic. The induction test will not detect antibiotics that affect DNA synthesis and its basis is obscure. To perform the induction test it is essential to add minimal salts such as $Ca^{2+}$ and $Mg^{2+}$ ions which are known to diminish or completely prevent the action of aminoglycosides (streptomycin, kanamycin, neomycin, erythromycin). In addition, the induction parameters are very strict. If samples contain other antibiotics (for instance nalidixic acid) or other substances triggering light production there may be problems in the interpretation of the results. The amount of bacteria in the test is a critical parameter. If the concentration of bacteria in the test is too high, the culture has to be aerated due to the absolute requirement of oxygen for the bioluminescence reaction in these bacteria. Additional problems include a great number of potential inducers, special measuring devices, and reproducibility of results.

The bacteriophage test can be utilized to detect antibiotics affecting DNA synthesis, transcription and translation. In this test, wild-type, light-emitting *P. phosphoreum* bacteria are infected with lytic bacteriophages. In the presence of an antibiotic, new infectious phages cannot be synthesized due to the fact that DNA-, RNA- or protein synthesis is blocked. In the presence of an antibiotic, the light emission is unchanged compared to the initial light level. However, if no antibiotic is present, the phages rapidly multiply and inactivate the host bacteria thus making it incapable of producing light. The bacteriophage test is difficult to perform since it is necessary to add phages (sometimes with different titers) to the assay mixture and the addition of antibiotic has to be carefully timed. The bacteriophage test suffers some of the same problems discussed with the induction test. Notably, the composition of assay mixture and the amount of bacteria used in the assay.

The methods discussed above can be used to reveal the presence of antibiotics generally but not to reveal individual antibiotics. By changing measuring conditions or by adding enzymes to degrade certain compounds, one is able to block the effect of some antibiotics. There is a great demand for fast and simple methods to detect heavy metals, toxins, or food additives. At the moment detection of these compounds must be performed in central laboratories. The devices for detecting heavy metals, toxins, or food additives are extremely expensive and need specially trained personnel to use them. Quick, qualitative tests performed in the field could screen for those samples which need more sophisticated instrumentation and research. Thus, the pressure on central laboratories would diminish and determination of problematic samples would be faster.

A commercial "Microtox" test is able to detect toxic substances from environmental specimens. This test is based on the use of light emitting *P. phosphoreum* bacteria. A sample to be analyzed is incubated together with bacteria and the presence of a toxic substance is evaluated from a decreased level of light produced by the bacteria when compared to controls. A severe drawback with this test is the need for high salinity (2%) by the organism. High salinity has been shown to decrease the biological effect of heavy metals. In addition, an incubation temperature of 15° C. can be an obstacle.

In addition to the Microtox test, several tests utilizing whole animals or animal cell lines have been developed to measure toxic substances. Pitfalls in these methods include complicated cultivation of cells, slow performance and a need for skilled personnel.

A test should be able to detect toxic and mutagenic substances from different waters such as from waste-, consuming-, raw- and groundwater and from water for refreshment purposes. In addition, water needed for industrial processes, food processes as well as raw water needed for pharmaceutical industry are of interest. The test should be able to evaluate samples from ground sediments and air for their toxicity and mutagenicity. The raw material used in food industry as well as quality control of food stuffs needs attention. From certain waters one should be able to detect the organic material which could be used for respiration and biosynthesis purposes by microbes contaminating the water. The organic material can be simple sugars, organic acids, peptides or proteins, compounds containing amino or phosphate groups linked to carbon chain etc. There is a need for rapid, non-expensive tests for these kind of compounds since the conventional methods take several days to complete in order to be able to evaluate the quality of water used for various purposes.

The invention described here is based on known and accepted principles of gene expression, the factors affecting gene regulation, and on the use of recombinant-DNA in organisms such as bacteria and yeast.

Gene technology has made it possible to use bacteria and yeast cells as hosts to produce proteins that these organisms do not produce naturally. Several kinds of recombinant-DNA vectors have been prepared for this purpose. Usually, the recombinant-DNA vectors are extrachromosomal plasmids. Recombinant-DNA plasmids can contain several genes and they can replicate independently of host chromosomal DNA. Recombinant-DNA techniques are utilized to transfer foreign genes into new host cells. The gene of interest can be cloned into a plasmid vector with restriction enzymes and DNA ligase. Following cloning, the recombinant-DNA plasmid is transformed into a bacterial host using methods well known in the art. For expression in a eukaryotic cell, the recombinant-DNA plasmid usually contains DNA from bacteria, viruses, and eukaryotes. Recombinant-DNA is transferred into eukaryotic cells using techniques well known in the art, such as calcium-phosphate precipitation or electroporation.

Many recombinant-DNA plasmids have been developed during the last few years where a gene of interest has been placed under control of a strong promoter. A goal has been to create high expression of a foreign gene in an organism such as *E. coli*. In an *E. coli* bacterium, the production of protein from the gene of interest can account for as much as 25% of the total cellular protein (Caulcott & Rhodes, 1986, Trends in Biotech., June, 142–146). Overexpression of a foreign gene can be deleterious to the host cell or its metabolism. To overcome the potential problem of overexpression, plasmids with regulatable promoters were developed, and the gene of interest is placed under the control of the regulatable promoter. The production of protein from the gene of interest can be turned on when the microbes achieve an optimal growth phase. Cultivation of the microbes to the optimal growth phase is performed under non-stressing conditions. Expression of the foreign gene is usually controlled by adding a chemical to the medium which activates the regulatable promoter. For example, plasmid pCSS108 (Korpella & Karp, Biotechnol Lett., 10(6), 1988, 383–388), shown in FIG. 6, contains a bacterial luciferase gene under the control of a regulatable promoter. Expression of bacterial luciferase is induced by isopropyl-β-D-thiogalactopyranoside (IPTG) added to the culture medium. In addition, physical parameters, such as an increase or decrease in incubation temperature might regulate protein production.

The plasmids commonly used contain one or more resistance determinants, with which to select from a large population of cells only those which contain the plasmid. The resistance determinants helps the cell to survive in circumstances which are poisonous to other cells. A selection agent is added to the growth medium and cells which contain the plasmid are able to grow, but cells which lack the plasmid are not able to grow. The resistance determinant is a gene which encodes a protein that degrades or otherwise inactivates the poisonous factor. Examples of such poisonous factors are antibiotics which are present in the growth medium. Several genes encoding resistance factors are known. The resistance factor used most often is the gene encoding β-lactamase. β-lactamase degrades penicillins or β-lactams which are penicillin derivatives. As a result of β-lactamase enzyme activity, the poisonous character of penicillin is lost and bacteria can grow. Other commonly used resistance genes include those encoding chloramphenicol acetyltransferase, kanamycin acetyltransferase and tetrahydrofolate reductase.

Depending on the type of cells chosen, genes which carry the ability for the cell to grow in the presence of tetracyclin, erythromycin, spectinomycin, streptomycin, sulfonamides, neomycin, thiostrepton, viomycin and colicins can also be used. Some resistance factors that eliminate or change the heavy metal present in the medium can also be used. Selection pressure in favor of a cell containing a plasmid can also be achieved by transferring a gene encoding a function which complements a growth defect in the organism. Normally, such growth defects arise from a defective gene in the chromosome of the organism. These genes are normally those which encode for proteins participating in an amino acid biosynthesis pathway. An essential amino acid is removed from the growth medium and the cell cannot grow unless the amino acid biosynthesis gene is present. The gene will be present in the cell if the plasmid is present. When the gene is expressed the amino acid biosynthesis pathway will be complemented and the cell can grow. The plasmids can also encode genes of other vital functions in the cell. An example of such genes include genes encoding proteins that participate in the formation of the cell wall.

The copy number of various plasmids inside the cell can vary from one to several hundred, to over a thousand. A plasmid often used, pBR322, has a copy number of about 60 whereas a derivative of it, pUC8, has a copy number of about 500. A reason for the large difference between two related plasmids is due to a one base pair mutation in the origin of replication (ori) sequence of the plasmid (Chambers et al., 1988, GENE, 68, 139–149). The copy number of a plasmid can be artificially increased at a suitable phase of growth by constructing a vector where ori is placed under the control of a strong and regulatable promoter. At present several plasmids are known whose copy number can be artificially shifted up during the growth of microbes. These plasmids are mainly used in industrial processes to produce foreign recombinant proteins in large quantities. Thus the use of these run-away replication vectors for purposes described above does not rule out the possibility of using them in this invention for measuring different agents which affect the cell. As examples in this invention we describe different run-away plasmids with which a change in copy number is possible. Run-away plasmids studied and used to produce foreign proteins belong to series pOU. The origin of replication region of pOU plasmids has been put under the control of strong and regulatable $P_R$ promoter of phage lambda (Larsen et al., 1984, GENE, 28, 45–54). The $P_R$ promoter of phage lambda is regulated by a repressor protein, cI857, which is destroyed by heating to 42° C. The protein can be produced from a lysogenic phage, i.e., a phage which is integrated in the chromosome of the host cell, from a plasmid where the coding sequence has been introduced or from another plasmid which belongs to a different incompatibility group. Plasmids of different incompatibility groups of are plasmids which are able to replicate independently without the presence of another plasmid in the same cell. When the repressor protein has been destroyed, $P_R$ promoter is turned on and without control it starts to produce proteins called copB and repA (originating from low-copy number plasmid R1) as well as transcription products of these and the copA gene. These factors and especially the overproduction of repA protein result in enhanced or even uncontrolled production of the plasmid DNA in E. coli bacterium.

Yeast as well as bacteria are single cell organisms but yeast differ from bacteria by being eucaryotic cells. Compared to higher eucaryotic cells yeast are far better characterized from the genetic point of view. The genetic maps of Saccharomyces cerevisiae and Schizosaccharomyces bombei are already known in great detail (Petes, 1980, Ann. Rev. Biochem., 49, 845–876). In addition, powerful methods to transfer genes into yeast are known. Thus, yeast are commonly used hosts for rec-DNA.

Four types of rec-DNA vectors are used with yeast: integration plasmids (YIp), episomal vectors (YEp), replicating vectors (YRp), and artificial chromosomes. The integrating vectors of yeast can contain DNA originating from bacteria and part(s) of yeast genes. This type of plasmid integrates exactly at certain point(s) in the yeast chromosome. The replicating yeast plasmids contain DNA from bacteria, part of yeast DNA and a specific area from yeast chromosome. The specific area from the yeast chromosome is responsible for the replication of the plasmid.

The specific area from the yeast chromosome permits the plasmid to replicate as extrachromosomal DNA molecule in the yeast cell. The episomal plasmids contain DNA from bacteria, a yeast gene and a part or the whole 2 micron plasmid of yeast (Hollenberg, 1982, Current Topics in Microbiology and Immunology, 96, 119–144). Artificial chromosomes are linear DNA vectors which are not well suited for expression of heterologous proteins.

A plasmid for yeast whose copy number can be regulated has been described. Centromeres are needed in yeast during the partition of a chromosome in mitosis and meiosis phases. Centromeric DNA (CEN3) has been extracted and transferred under the control of alcohol dehydrogenase promoter (ADH2). The ADH2 promoter is repressed by glucose. The action of a CEN3 plasmid can be controlled by the carbon source used to cultivate yeast. When glucose is used as carbon source the ADH2 promoter is repressed and CEN3 works normally by balancing the plasmid structure (YRp) during mitosis. If the carbon source in the growth medium is changed the plasmid starts to replicate and the copy number can increase up to one hundred per yeast cell (Chlebowicz-Sledziewska, E. & Sledziewska, A., 1985, GENE, 39, 25–31).

The expression vectors used in yeasts normally contain the following strong regulatable promoters: alcohol dehydrogenase isoenzyme I (ADHI) gene promoter, phosphoglycerol kinase (PGK) promoter, repressible acid phosphatase (PHO5) promoter and the promoter for α-factor. ADHI is a yeast cytoplasmic enzyme. ADHI produces ethanol from acetaldehyde and needs NADH as a cofactor. When yeast cells are cultivated in the presence of glucose there is at least 1% ADHI protein from the total amount of proteins in yeast. The PGK promoter can be controlled by the carbon source (for example glucose) used. The expression of PHO5 can be prevented by the addition of inorganic phosphate and activated by eliminating inorganic phosphate from growth medium. The control of PHO5 happens through a special regulation apparatus, which is formed from PHO2, PHO4, PHO80 and PHO85 gene products (Bosfiana, K. A., 1980, Proc. Natl. Acad. Sci. USA, 77, 6541–6545). Some mutants (PHO4 and PHO80) are known, which can be activated by a simple change in temperature. These mutant yeast cells grow at 35° C. and do not produce acid phosphatase enzyme even if inorganic phosphate is absent in the medium. If the cultivation temperature is shifted down, acidic phosphatase is produced efficiently whether there is phosphate or not in the medium. This system to control the protein production by a change in the cultivation temperature has been used to produce, for instance, interferons (Kramer et al., 1984, Proc. Natl. Acad. Sci USA, 81, 367–370).

The use of higher eucaryotes as host cells for rec-DNA vectors to produce foreign proteins is rapidly expanding. The goal of such use is to produce proteins of eucaryotic origin in large quantities. In an optimal expression system it would be possible to produce proteins in several different types of cell lines. A fully regulatable expression system for protein production would be an ideal solution. The regulatable promoters used most often work only in certain host cell systems. The regulation of these promoters is poor and the expression vectors are based on DNA of tumor producing viruses, thus there also exists certain risks in their uses.

In higher eucaryotes gene expression can be regulated with the help of the following: simian virus (SV40) T-antigen, metallothionein genes, heat-shock genes, glucocorticoid hormones, DNA methylation or with anti-sense RNA. The antigen produced by SV40 controls its own transcription. T-antigen is produced in large amounts immediately after the virus has infected the target cell. Later the T-antigen binds to its own promoter and prevents transcription. If SV40-vectors are used for cloning, regulation of the T-antigen can be prevented by using a suitable temperature sensitive T-antigen mutant. In these cases T-antigen mutants produce T-antigen normally at high temperatures but the production is prevented at room temperature (Rio et al., 1985, Science, 227, 23–28).

Metallothioneins are proteins which bind heavy metals. Many eucaryotic cells produce these proteins in the presence of heavy metals. It has been estimated that there is an increase over fifty fold in the production of metallothioneins when cadmium is added to the growth medium to a concentration of $4 \times 10^{-6}$ molar (Hamer, D. H. & walling, M. J., 1982, J. Mol. Appl. Genet., 1, 273–288). The protein production induced by cadmium can be further increased by using low $Cd^{2+}$-content growth media.

Many promoters of heat-shock genes have been shown to be applicable and well regulated in several different cell lines. The regulation of these promoters is performed simply by shifting the growth temperature. The genes are activated at high temperatures and produce proteins. At low temperatures the proteins are produced in low amounts or not at all. The best studied example is the heat-shock system of common fruit-fly, Drosophila melanogaster, in which a rise in temperature from 25° C. to 37° C. causes the cessation of normal protein production and the heat-shock proteins start to emerge. A major heat-shock protein is hsp70. The regulation mechanisms of heat-shock protein expression are not well known. By using heat-shock promoters (hsp70), it has been possible to increase the production of hGH (human growth hormone) up to 1200-fold compared to unactivated cells (Dreano et al., 1985, GENE, 49, 1–8).

The invention described here uses procaryotic and eucaryotic organisms, which have been carefully selected and which contain applicable rec-DNA vector constructions. By turning on the synthesis of DNA, RNA or proteins under strict control one is able to measure or detect either directly or indirectly all those factors which affect on the synthesis machineries described above. As the basis of measurement one can use the protein product encoded by the rec-DNA vector, the marker protein or its activity or the overall metabolic activity. By activating the replication of rec-DNA vector in a controlled fashion one is able to measure the amount of DNA formed directly by using radioactive labels or with flow-cytometric techniques.

One is able to prepare suitable rec-DNA vectors for the measurement of different classes of chemicals depending on the target of the chemical. It is possible with the aid of *E. coli* bacteria containing runaway-replication type plasmids to quantitate, for instance, compounds inhibiting DNA synthesis (nucleotides) and DNA replication as well as those compounds binding to DNA like several cancer drugs. Replication of runaway-replication plasmids is controlled, for instance, by an inducible promoter, $P_{RE}$, of phage lambda. Thus, DNA synthesis and the replication of a plasmid can be triggered at a predetermined point of time. The analytes to be measured can be linked directly to this regulatable and strong DNA biosynthesis which is not dependent on cell division. If the synthesis or replication of DNA is inhibited the result is seen in the copy number of plasmid. The copy number may be the same or even decreased compared to the initial stage. In the uninhibited control cells the copy number of plasmid per cell may increase rapidly. The change in copy number can be measured either directly by measuring the amount of DNA or indirectly by measuring the amount of gene products or the activity encoded by the plasmid DNA. It is possible to determine agents that have very different mode of action on the cell with the aid of this kind of a plasmid. This is due to the fact that one can also engineer a gene encoding a marker protein under the control of a strong and regulatable promoter, the expression of which is measured in the test. Thus everything affecting DNA, RNA, proteins, or their biosynthesis can be measured. If one wants to develop a broad range of tests which covers agents affecting cell wall, nucleic acids, proteins and metabolism an ideal means of detecting these agents is based on this kind of a runaway-replication plasmid. In these cases cells are allowed to replicate after which the promoter regulating the replication is activated. Simultaneously, or after a certain period, the promoter regulating a gene encoding a marker protein is activated. A vector with similar characteristics can be developed for eucaryotic cells.

Another kind of approach is to use plasmids whose replication is tied to host cell division. Rec-DNA multicopy plasmids in which the gene encoding the marker protein is under the control of a strong and regulatable promoter can be used to detect agents that affect cell membranes, proteins and metabolism. Agents affecting DNA or cell membranes can be detected with the system if actively dividing cells are used. The multicopy plasmid is synthesized for daughter cells and the system is sensitive to agents affecting DNA. Actively dividing cells are also sensitive to agents affecting the cell membranes. If the strong promoter regulating the expression of the marker protein is activated the system ill then also be sensitive to agents affecting the mRNA and protein synthesis.

As a special application, when genes encoding luciferase are used, one can determine agents that affect energy metabolism. This is due to the fact that the reactions catalyzed by luciferases use energy-rich substances of cells. Agents that can affect the energetic state of the cell on all biosynthetic levels (replication, transcription and translation) or in metabolism, can be determined with the aid of bioluminescence, i.e., formation of light emission by the cells. A special case is bacterial luciferase, which uses central products of metabolism, NAD(P) and $FMNH_2$. Another special case is fire-fly and click beetle luciferases, which use a central metabolite, ATP, for light production.

The nature of the invention described here makes it possible to use very different kinds of measuring modes for example spectrophotometric, fluorometric, luminometric and visual methods. Spectrophotometric methods can be an alternative when there is a gene cloned into plasmid whose product can be measured by monitoring the change in color such as β-galactosidase, alkaline phosphatase, amylases, peroxidases, glucuronidases or oxidoreductases. Fluorometric methods utilize fluorescent substrates developed for various enzymes, thus yielding somewhat greater sensitivity compared to spectrophotometric techniques. The luminometric method is performed with the aid of genes encoding either bacterial or beetle luciferases. Several luminescent bacterial species exist such as *V. harveyi, V. fischeri, P. leiognathi, P. phosphoreum, Xenorhabdus luminescens* etc. Examples of luminescent beetles are *Luciola minarelica, Photinus pyralis, Pyrophorus plaaiothalamus* etc. There several eucaryotic species in the sea which luminesce, such as marine ostracod *Vargula hilgendorfii*, jellyfish *Aeguorea victoria*, batrachoidid fish *Porichtys notatus*, pempherid fish *Parapriacanthus ransonneti* etc., which could be useful in the future for various applications. Here an advantage over spectrophotometric and fluorometric measurement is the extremely sensitive detection of light emission. An important benefit in luminescent methods is the possibility to calibrate internally the measurements by using other intracellular genes which encode luciferase emitting a different color which could be measured with a special two wavelength-detecting apparatus. The other gene can be cloned in the same rec-DNA vector, in another vector belonging to a different incompatibility group, inserted in the host chromosome, or in a phage etc. An example is the click beetle luciferases, which emit four different colors. The wavelengths range from 547 nm to 593 nm (Wood et al., 1989, Science, 244, 700–702). The other gene resulting in different wavelength can be put under an inducible production system (indicator "gene") or it can be expressed constitutively (internal standard) to compensate possible secondary effects arising from heterologous samples. The use of a simple color indicator is useful in cases where there is no need for high sensitivity but where the simplicity and fast performance are more important. If the changes in cell metabolism are to be detected one can use for example tetrazolium salts which form a low-solubility formazan color when reduced. In these cases genes encoding dehydrogenases or oxidoreductases act as mediators of reducing quantities to yield the intense color of formazan. Also immunological methods (antibodies) coupled to sensitive measuring systems (RIA, FIA) are possible. Use of radioactive labels and flow cytometry in detecting the end point of the test are possible.

BRIEF DESCRIPTION OF THE FIGURES

FIG. 5d shows genetic organization of plasmid pCSS305.

FIG. 7b shows genetic organization of plasmid pCSS301.

FIG. 8 shows the quantity and quality of plasmid DNA extracted from heat-treated *E. coli* cells incubated in the presence of nalidixic acid.

FIG. 9b shows the detection of chloramphenicol using *E. coli* cells cloned with pCSS123.

FIG. 9c shows the detection of heavy metal, cadmium, using *E. coli* cells cloned with pCSS123.

FIG. 9d shows the detection of trimethoprim using *E. coli* cells cloned with pCSS123.

FIG. 9e shows the detection of oflaxicin using *E. coli* cells cloned with pCSS123.

FIG. 9f shows the detection of UV light using *E. coli* cells cloned with pCSS123.

FIG. 9i shows the detection of citroflaxicin using *E. coli* cells cloned with pCSS305.

FIG. 9j shows the detection of oflaxacin using *E. coli* cells cloned with pCSS305.

FIG. 10 shows a comparison of the detection of toxic substances in *E. coli* cells where protein synthesis is directed by the $P_L$ promoter or the lac promoter.

FIG. 11b shows the detection of ampicillin, oxytetracyclin, and streptomycin using *B. subtilis* 1A40 cells cloned the luciferase gene from click beetle (pCSS962).

FIG. 13 shows the detection of oxytetracyclin.

The method based on the change in copy number of rec-DNA vector

A cell builds its heritable material, DNA, from deoxyribonucleotides. Extrachromosomal or episomal DNA can exist as plasmids in the cell. The replication of the plasmids is not directly dependent on cell proliferation. Each plasmid has its own origin of replication to replicate and divide into daughter cells in the course of cell division. However, the plasmid utilizes the host cellos DNA replication machinery for its own replication.

Figure 1:
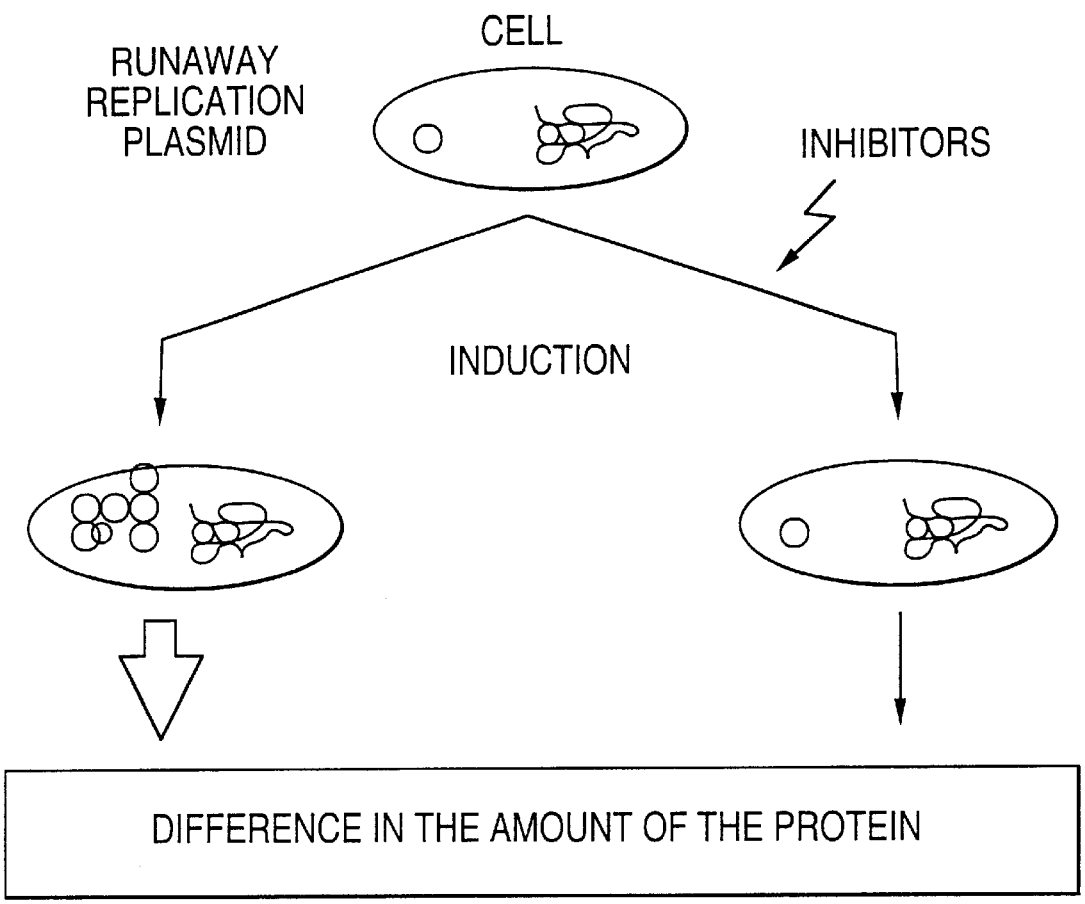
FIG. 1 shows a schematic representation of a method based on a change in plasmid copy number.

FIG. 1 shows a schematic representation of a method based on the change in plasmid copy number. A cell contains a special plasmid (for example runaway-replication plasmid pCSS123) which can be induced to replicate at a predetermined point of time and in a controlled fashion. In the beginning, the cell contains only few copies of the plasmid. The agent to be examined is allowed to affect the cell for a suitable period of time, after which, the replication of the plasmid is initiated. The plasmid will then replicate as much as possible in the presence of the agent. The replication of the plasmid can be triggered by adding a coupling chemical or by physical means, for example, shifting the temperature high enough for replication to commence. Simultaneously or after triggering the replication, the expression of the marker protein can be turned on from the same special plasmid. In this case the degree of the plasmid replication can be directly quantitated by measuring the amount of the marker protein or its activity which is dependent on the copy number of the plasmid inside the cell. This has been described in FIG. 1 as an amount of enzyme activity produced by the plasmid encoded gene. This makes it possible to study and measure factors affecting the synthesis of RNA, transcription, translation, cell walls, specific metabolic pathways and enzyme activities.

Figure 2:
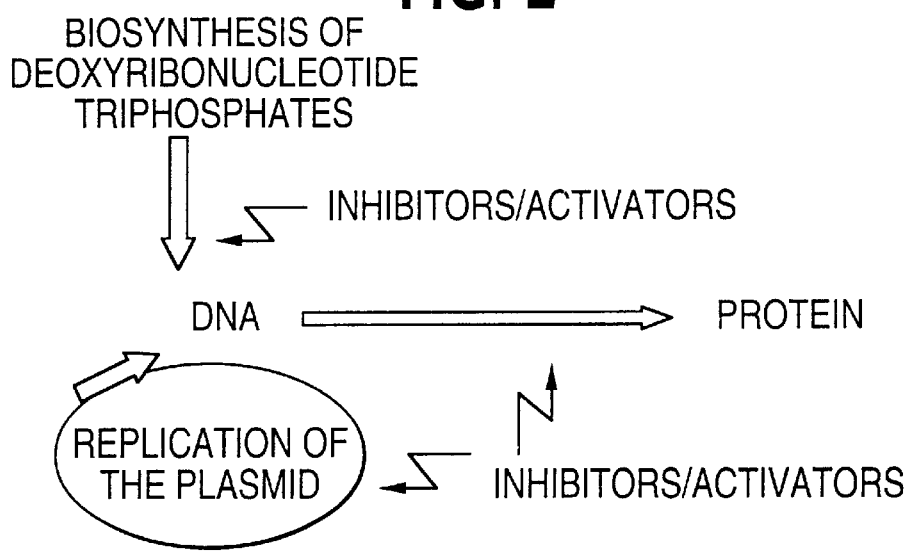
FIG. 2 shows a schematic representation of possible effects different agents will have on the cell and how the effects can be coupled to a change in plasmid copy number.

Shown in FIG. 2, a schematic representation on the possible effects different agents will have on the cell and how the effects can be coupled to a change in plasmid copy number. The biosynthesis of DNA, RNA and protein are multistep processes and they need the cooperation of several factors. Each step has both natural and artificial agents which affect the systems either by activating or inhibiting them. For instance, nalidixic acid has an effect on the replication of DNA by inhibiting the action of DNA polymerase.

Remarkably, the starting point is a few regulatable DNA molecules which can be induced to replicate without cell proliferation. This makes it possible to use non-proliferating cells for the testing of effectors. Thus, the time used for the assay is not limited by the slow growth and proliferation of cells. The inventiveness of this method is based on controlled multiplication of the plasmid DNA and therefore on a possibility to investigate very large groups of compounds.

In the instant invention, advantage is taken of regulatable promoters and the machineries controlled by these promoters to increase the copy number of a plasmid and/or production of a marker protein by the cell at a predetermined phase of growth. In this context, promoter means an area of DNA where the enzyme RNA polymerase can bind, and where special regulator proteins or other molecules can interact. Promoters can control the expression of a gene beside the promoter or nearby the promoter. Examples of inducible E. coli promoters include lac, trp, hybrid promoter tac, and lambda promoters $P_L$ and $P_R$. These promoters differ in strength and in mode of induction. Promoters lac and trp can be induced with chemicals whereas induction of $P_L$ promoter can be induced by heat treatment.

Determination of Toxic Substances using a Method where Protein Biosynthesis is Controlled by a Regulatable Promoter in rec-DNA Plasmid In a cell, RNA, especially messenger RNA (mRNA), also contains information. Messenger RNA is synthesized from ribonucleotide triphosphates. The ribonucleotide triphosphates are stored in the cell. Messenger RNA is synthesized according to each gene in the DNA. Special transcription machinery contains molecules responsible for the transcription of DNA into RNA. Proteins are made according to mRNA-molecule templates using universally accepted principles. RNA synthesis and the corresponding protein production encoded by the mRNA can be switched on very quickly. Special rec-DNA plasmids are used in the instant invention. The special rec-DNA plasmids have been prepared so they can be activated and produce large amounts of selected proteins. For this purpose, a special plasmid has been constructed so the plasmid copy number is constant in certain host cells. The plasmid copy number cannot be selected in other host cells. The plasmid used should be high copy number. High copy number plasmids correspond to high protein production as more copies of the gene are present. As cells containing the special rec-DNA plasmids are treated with agents prior to induction, the amount of agent, mode of action, or overall presence in the system can be determined by measuring protein production and determining if protein production is altered. Agents include, for example, antibiotics which affect mRNA synthesis or antibiotics which affect protein synthesis. Utilizing the method described herein, agents can be identified which specifically affect and control biosynthetic routes. Using rec-DNA plasmids as described herein, agents can be identified on which selected protein production is dependent.

Remarkably, agents which affect DNA synthesis and cell membranes can be identified with the methods described herein. This is possibly due to the fact that when a microbe is proliferating it is forced to synthesize these high-copy number plasmids and hence these special plasmids are susceptible to agents which affect DNA synthesis. Actively proliferating cells are especially susceptible to agents that act against cell membranes and their biosynthesis.

Figure 3:
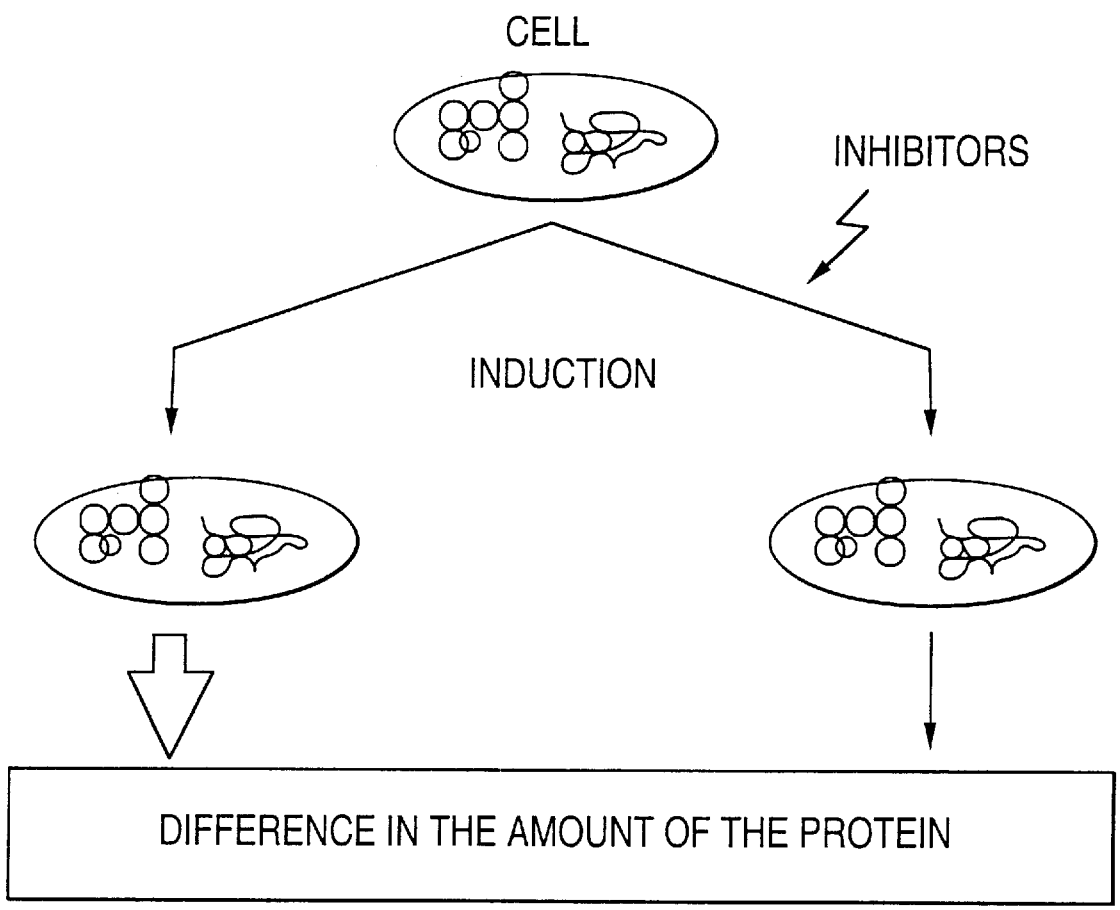
FIG. 3 shows a schematic representation of the efficiency of mRNA and protein synthesis in a cell exposed to an agent inhibiting biosynthesis.

FIG. 3 shows the practical performance of the invention described above in a case where the special plasmid exists at high copy number in the microbe. The microbe was exposed to an agent inhibiting biosynthesis and after a period of time the special plasmids were activated to produce protein. In this example the protein is an enzyme. The thickness of the arrows shown in FIG. 3 correspond to the efficiency of mRNA and protein synthesis, and thus also to the efficiency of the agents. When the inhibiting agent was present, production of the enzyme remained low. This contrasts with the case where the affecting agent was not present or there were known amounts of the agent.

Figure 4:
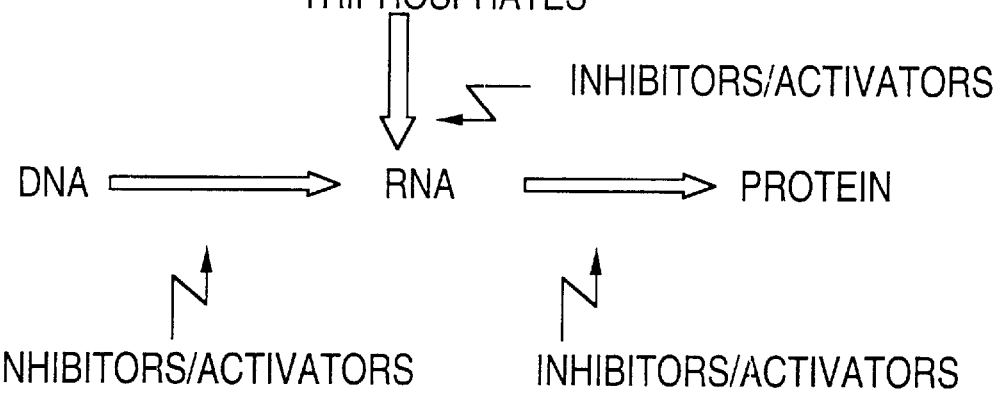
FIG. 4 shows biosynthetic routes which can be affected if proliferating cells are utilized.

FIG. 4 shows those biosynthetic routes which can be affected with the rec-DNA plasmid described above if proliferating cells are used. If one uses actively proliferating cells in the measurement, it is also possible to study agents affecting DNA as is shown in FIG. 2. The difference from FIG. 1 is the initial amount of plasmid copies in the cell and the possibility of artificially elevating the copy number in non-proliferating cells.

Promoters exist which can be induced by suitable treatments. The strength of promoters varies and the promoters described in this invention are rather strong. However, the $P_L$ promoter is stronger than the lac or trp promoters. The $P_L$ promoter of phage lambda is also much faster, i.e., the effect of induction is clearly seen much earlier when compared to the lac or trp promoters. The slow induction rate of the lac and trp promoters can be partly explained by the slow uptake of the inducing molecule through the cell membranes. Further, the rate of induction is affected by the rate at which the inducer transits the inside of the cell to its effector site. In addition, the copy number of the plasmids also causes relative differences in the induction rate. The copy number of plasmid pCSS112 (see FIG. 7) in E. coli is about 60, whereas plasmid pCSS108 (see FIG. 6) has a copy number of around 600. The production of bacterial luciferase by the plasmids is controlled in pCSS112 by the $P_L$ promoter of phage lambda and in pCSS108 by the lac promoter of E. coli lactose operon. Both promoters are controlled by certain repressor proteins, which are produced in limited amounts. As the copy number of plasmid in the former case is ten times lower than in the latter case, the production of luciferase protein is better shut down, i.e., repressed. In the latter case, the lac promoter leaks due to the relatively low amount of repressor protein and thus the basal level of the luciferase protein is already at a high level. The effect of toxic substances can be shown more effectively when a strong and fast-induced promoter is used to regulate a certain gene or action in a rec-DNA vector.

The Bacterial Strains, Plasmids and their Construction, Methods used in the Invention As cloning hosts and in toxicity measurements E. coli JM 103 (lac-pro, thi, strA, supE, enda, sbsB15, hsdR4 (F'traD34, proAB, lacI$^q$Z M15) (Messing et al., Nucl. Acids Res., 9, 1981, 309–321), MC1061 (cI$^+$, araD139, (ara-leu) 7696, lacX74, galU$^-$, galK$^-$, hsr$^-$, hsm$^+$, strA) (Casadaban & Cohen, J. Mol. Biol., 138, 1980, 179–207), BW322 (CGSC, rfa-210: :Tn10, thi-1, relAl, spoT1, pyrE) and K-12 (M72 Sm$^R$-lacZam bio-uvrB, trpEA2 (Nam7Nam53cI857 HI) (Remaut et al., 1981, GENE, 15, 81–93) and *Bacillus subtilis* 1A40 (Bacillus Genetic Stock Center, lys-3, metB10, trpC2) were used. Cells were grown on appropriate minimal agar plates and were kept maximally one month at +4° C. after which new plates were streaked. The strains were also kept in 15% glycerol at −70° C., wherefrom growth was initiated on minimal plates. Cells for plasmid extraction were first cultivated in 5 ml of 2×TY medium (16 g Bacto tryptone, 8 g Yeast extract, 8 g NaCl, H$_2$0 to 1 l, pH 7.4, with appropriate antibiotic) 10 h at 30° C. in a shaker after which the culture was transferred to a larger volume for 10 h in the same medium.

Figure 5A:
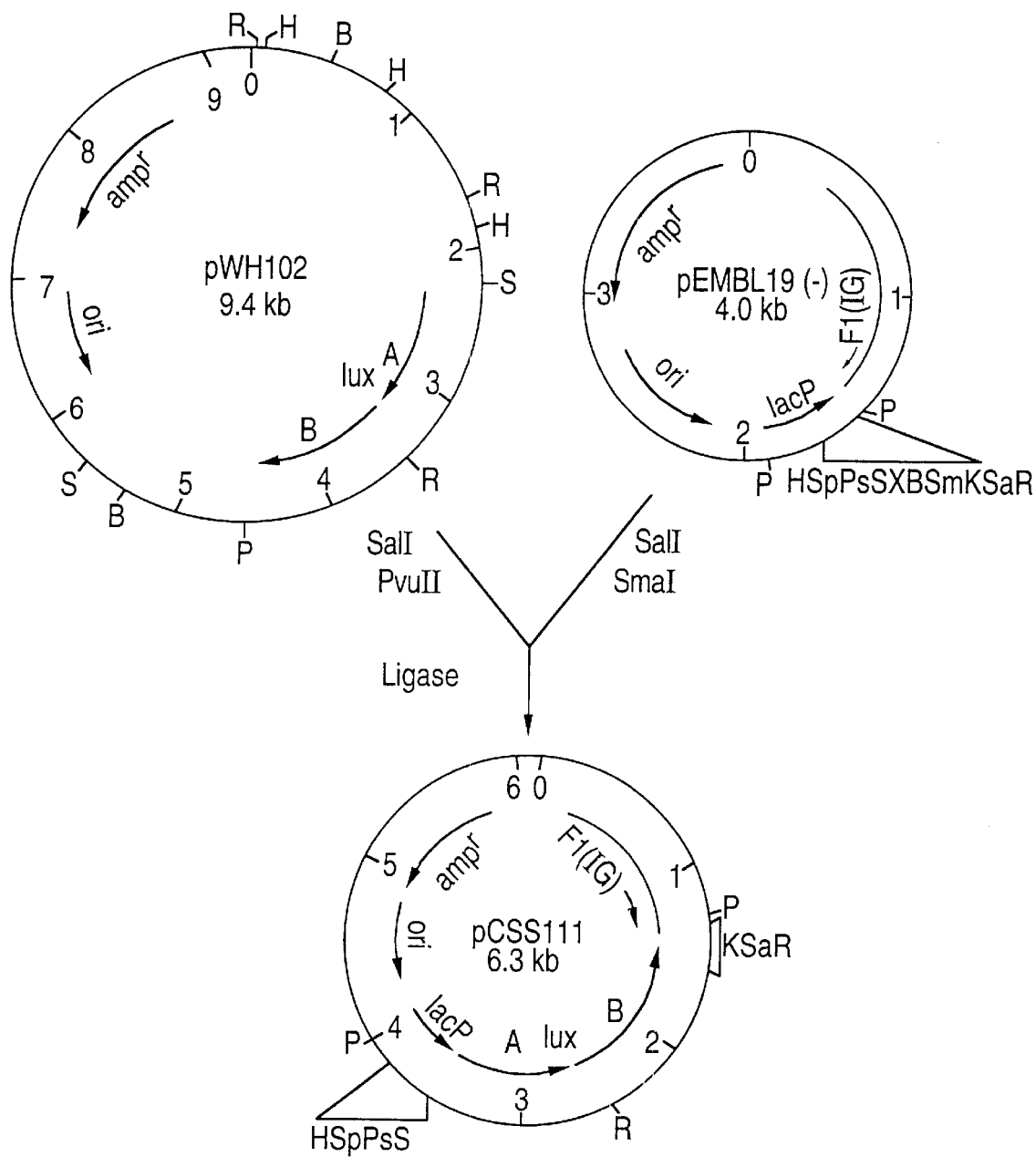
FIG. 5a shows construction of plasmid pCSS111.
Figure 5B:
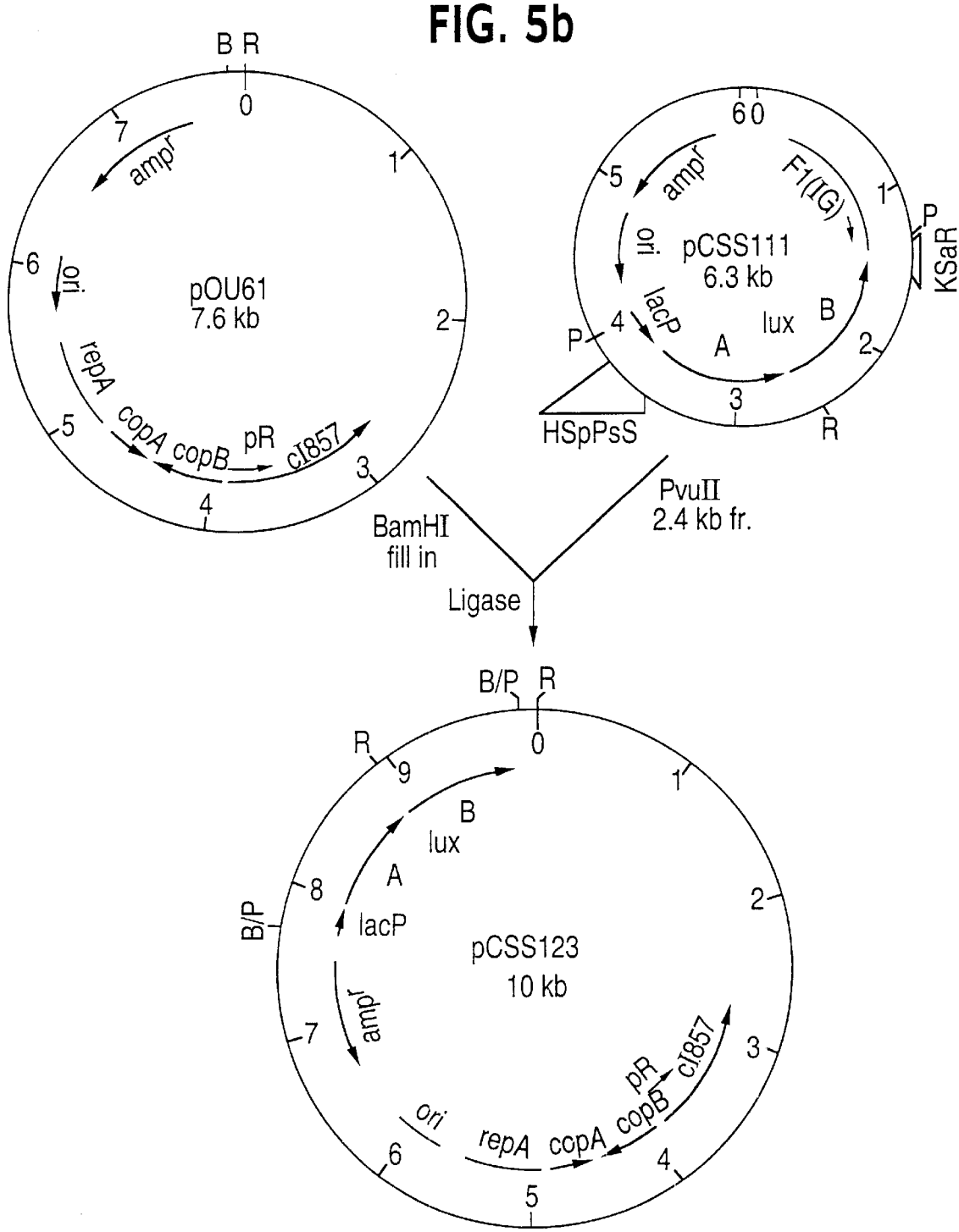
FIG. 5b shows construction of plasmid pCSS123.
Figure 5C:
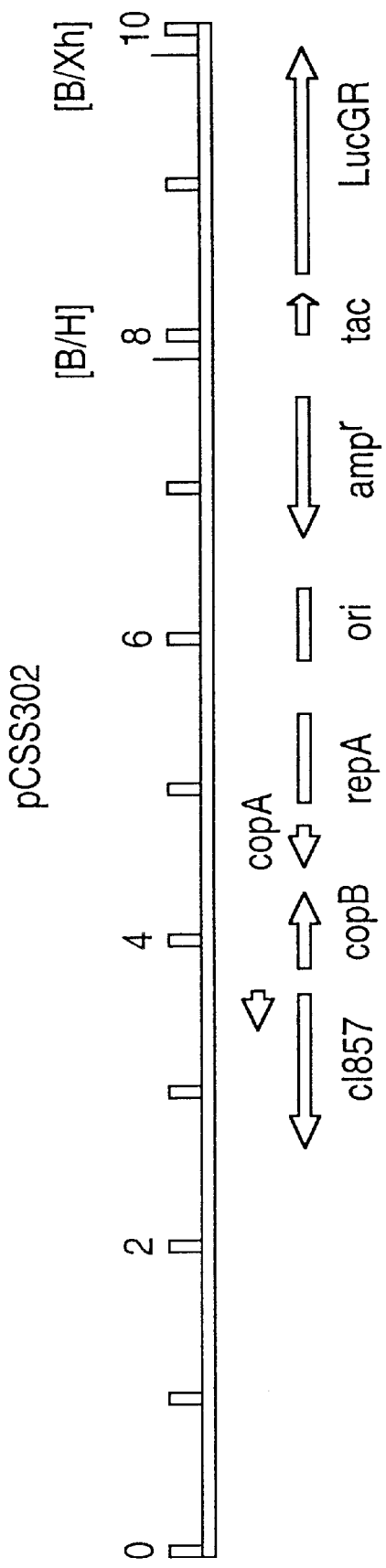
FIG. 5c shows genetic organization of plasmid pCSS302.

FIGS. 5a and 5b shows the construction of a rec-DNA plasmid pCSS123 (deposited with Deutsche Sammlung von Mikroorganismen und Zellkulturen GmbH (DSM), Mascheroder Weg 1 B, D-3300 Braunschweig, under the Budapest Treaty on Jan. 2, 1989, with a DSM number 5119), in FIG. 5c the construct of a rec-DNA plasmid pCSS302 deposited with DSM under the Budapest Treaty on Mar. 3, 1993, with a DSM number of 7503, and in FIG. 5d the construct of a rec-DNA plasmid pCSS305 deposited with DSM under the Budapest Treaty on Mar. 3, 1993, with a DSM number of 7504. Plasmid pWH102 (Gupta et al., 1985, Arch. Microbiol., 143, 325–329) was cut with the restriction enzymes SalI and PvuII and fragments were separated by agarose gel electrophoresis. A DNA band of 2300 base pairs (bp) was cut out of the gel under UV light. The low-gelling temperature agarose was melted at 65° C. and the DNA band was ligated with DNA ligase to plasmid pEMBL19(−) (Dente et al., 1983, Nucleic Acids Res., 11, 1645–1655) cut with SalI and SmaI. The plasmid obtained was transformed into E. coli JM103 cells using a method described below. A plasmid extraction in mini-scale was performed according to Maniatis et al. (1982, Molecular Cloning: A Laboratory Manual, Cold Spring Harbor Laboratory, Cold Spring Harbor) and the correct constructions were verified with suitable restriction enzyme analysis. Plasmid extraction in large scale was performed according to the same manual. The plasmid shown in FIG. 5a (pCSS111) was cut with the restriction endonuclease PvuII and a DNA-piece of 2400 bp was separated as described earlier. This piece, containing bacterial luciferase genes from *V. harveyi* under lac promoter control, and was ligated to plasmid pOU61 (Larsen et al., 1984, GENE, 28, 45–54) which was cut with the restriction enzyme BamHI and filled in with Klenow DNA-polymerase enzyme. Ligation mixture was transformed to E. coli JM101 strain as described below and correct plasmid containing colonies were picked by their ability to produce light after visual checking of the plates in a dark room. This was performed by adding 5 µl of 10% decanal on the lid of cultivation plate, which revealed the light producing colonies within a few minutes after the aldehyde had penetrated the cells. The plasmid obtained is shown in FIG. 5b and was named pCSS123. An analogous runaway-replication plasmid pCSS302 was constructed as follows: plasmid pLucGR (tac) (Wood et al., 1989, Science, 244, 700–702) was cut with the restriction endonucleases XhoI and HindIII and filled in with Klenow enzyme. After separation of the fragments in an agarose gel, a 1800 bp fragment containing the gene encoding green luciferase of click beetle under the control of tac promoter was ligated to plasmid pOU61 which was cut with BamHI and filled in as described above. Ligation mixture was transformed in E. coli JM103 and correct transformants were verified from plasmid minipreparations and the resulting plasmid pCSS302 is shown in FIG. 5c. A second analogous runaway-replication plasmid pCSS305 was constructed as follows: plasmid pCGLS11 (K. Nealson, personal communication and in press) was digested with the restriction enzyme PvuII and a 7 kb fragment containing the genes encoding luciferases α- and β-subunits of *X. luminescens* under the control of lac promoter of E. coli were ligated to plasmid pOU61 which was cut with BamHI and filled in as described above. Ligation mixture was transformed in E. coli JM103 and correct transformants were verified from plasmid minipreparations.

The symbols and abbreviations used: amp$^r$=gene encoding β-lactamase, ori=the origin of replication of the plasmid, luxA and B=genes encoding the subunits of luciferase, lacp=the promoter of the E. coli lactose operon, F1(IG)=the intergenic region of phage F1, MCS=multible cloning site of pUC18 (Yanisch-Perron et al., 1985, GENE, 33, 103109), kb=thousand base pairs, repA, copA and cobB=genes encoding proteins responsible for plasmid copy number and partitioning of plasmid into daughter cells, and cI857=the temperature sensitive repressor of phage lambda. The abbreviations of restriction endonucleases used: R=EcoRI, H=Hindiii, B=BamHI, S=SalI, P=PvuII, Sa=SacI, K=KpnI, Sm=SmaI, X=XbaI, Ps =PstI, Sp =SphI. B/P=the ligation point BamHI, filled in, PvuII. B/H=ligation point BamHI, filled in, HindIII. B/Xh=ligation point BamHI, filled in, XhoI.

Figure 6:
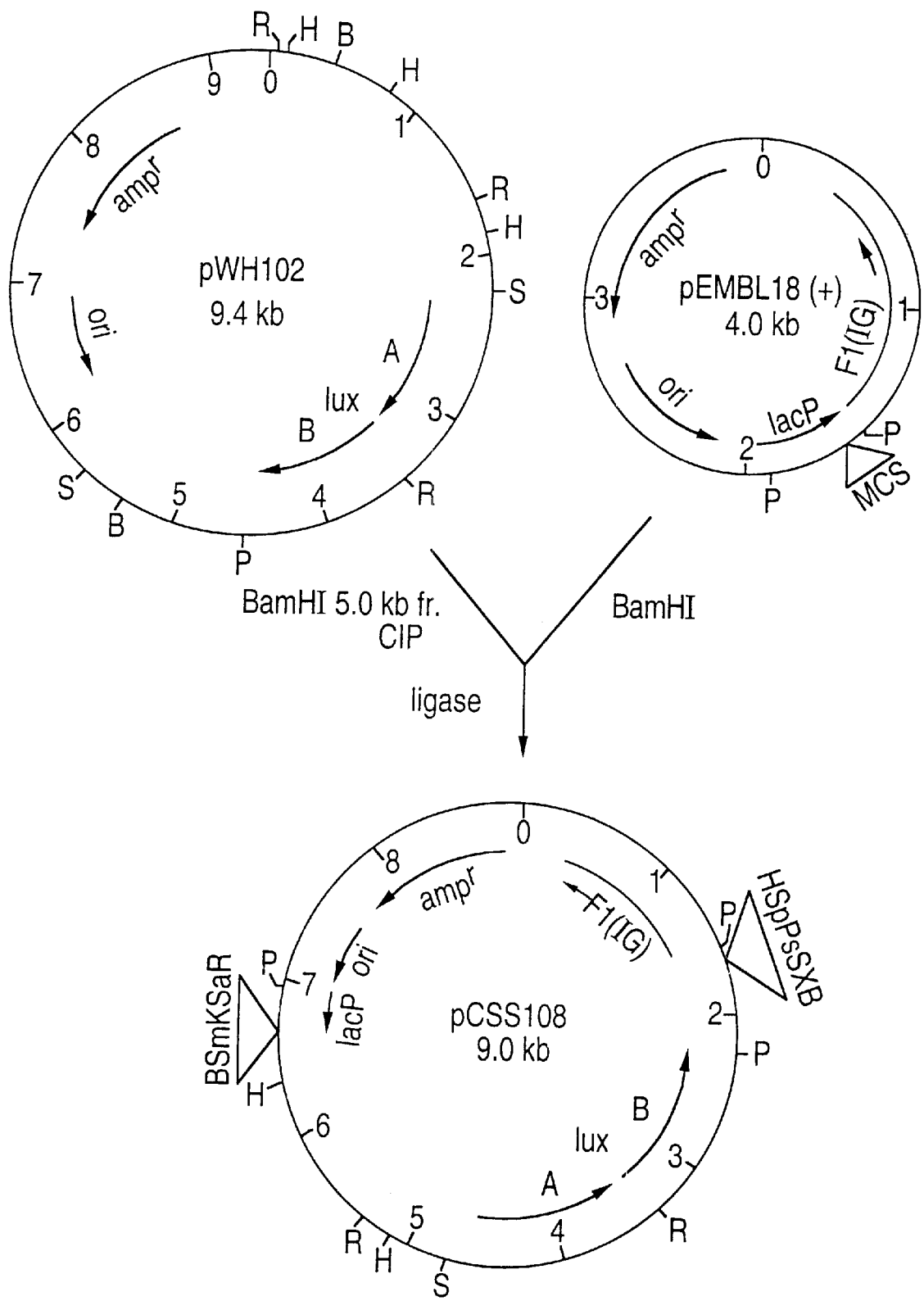
FIG. 6 shows construction of plasmid pCSS108.

FIG. 6 shows plasmid pCSS108 (Korpela & Karp, Biotechnol. Lett., 10, 1988, 383–388), which is used for production of bacterial luciferase by adding a chemical called IPTG. IPTG triggers protein production by binding to lac repressor protein. The genes encoding luciferase from Vibrio harveyi were transferred from the plasmid pWH102 (Gupta et al., 1985, Arch. Microbiol., 143, 325–329) by cutting the plasmid with the restriction enzyme BamHI. The two pieces obtained were treated with enzyme alkaline phosphatase (CIP) to remove the terminal phosphate groups so that the pieces can not ligate to themselves. A piece of 5000 bp was separated in an agarose gel as described previously. This fragment was ligated using T4-DNA ligase to a plasmid pEMBL18(+) which had been cut with the same enzyme. After transformation to E. coli JM103 and overnight incubation of the transformants, the cultivation plates were screened for light producing colonies as described above. Symbols used are as in FIG. 5.

Figure 7A:
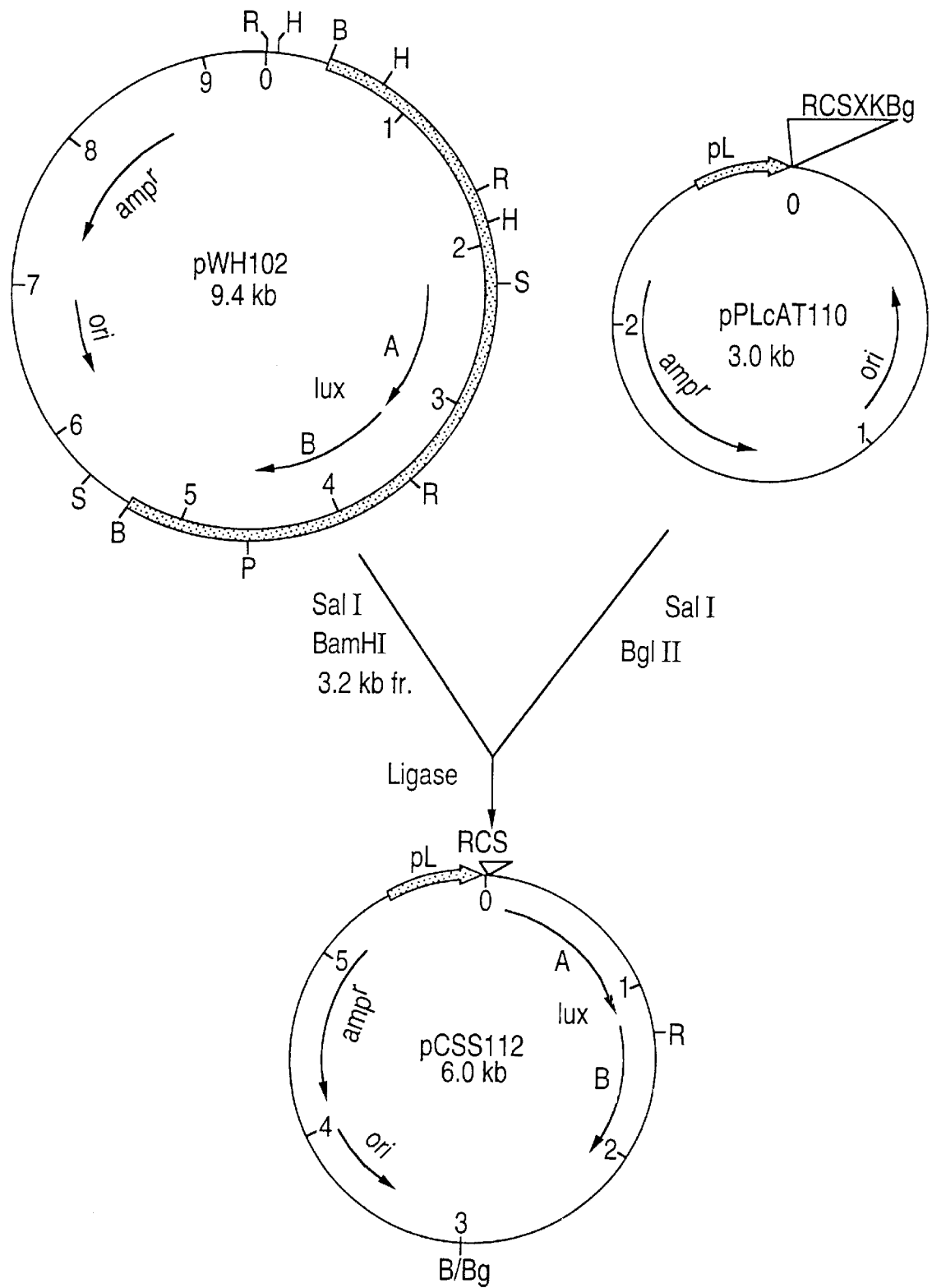
FIG. 7a shows construction of plasmid pCSS112.

The construction of plasmid pCSS112 (deposited as a DSM number 5120) is shown in FIG. 7a. The plasmid contains luciferase genes from V. harveyi and the genes are under the control of the $P_L$ promoter of phage lambda. The promoter is regulated by the repressor protein cI857 of phage lambda. When cultured in a suitable bacterial host such as E. coli K-12 HI trp, the repressor protein can be destroyed by heat treatment. Plasmid pWH102 was cut with restriction enzymes SalI and BamHI. Plasmid pPLcAT110 (Stanssens et al, 1985, GENE, 36, 211–233, partly unpublished) was cut with restriction enzymes SalI and BglII. The DNA fragments were separated as described earlier and a 3200 bp piece from plasmid pWH102 and a 2900 bp piece of pPLcAT110 were ligated with the aid of T4-DNA ligase. After transformation into E. coli MC1061 (cI$^+$) the correct plasmid containing transformant was screened as described above. The plasmid obtained was transformed to E. coli K-12 HI trp host. FIG. 7b shows a plasmid pCSS301 which is basically similar to pCSS112 except a gene encoding green click beetle luciferase (Wood et al., 1989, Science, 244, 700–702) is present. A plasmid pLucGR(tac) containing the luciferase gene from click beetle was digested with restriction enzyme BspHI, the cohesive ends were made blunt by Mung bean nuclease treatment and a DNA fragment of 1643 bp was separated in an agarose gel as described. This fragment was ligated to XbaI-BglII—digested vector pPLcAT110 (described earlier), which was filled in and CIP-treated. The ligation mixture was first transformed to E. coli MC1061 cells and after the correct plasmid was found from plasmid minipreparations it was transformed to E. coli K-12 HI trp. The symbols used are as in FIG. 5, also $P_L$=leftward promoter of phage lambda., Pv=PvuI, Xb/Bs=ligation point XbaI, filled in, BsphI, Mung bean treated, Bs/Bg=ligation point BsphI, Mung bean treated, BglII, filled in.

Figure 7C:
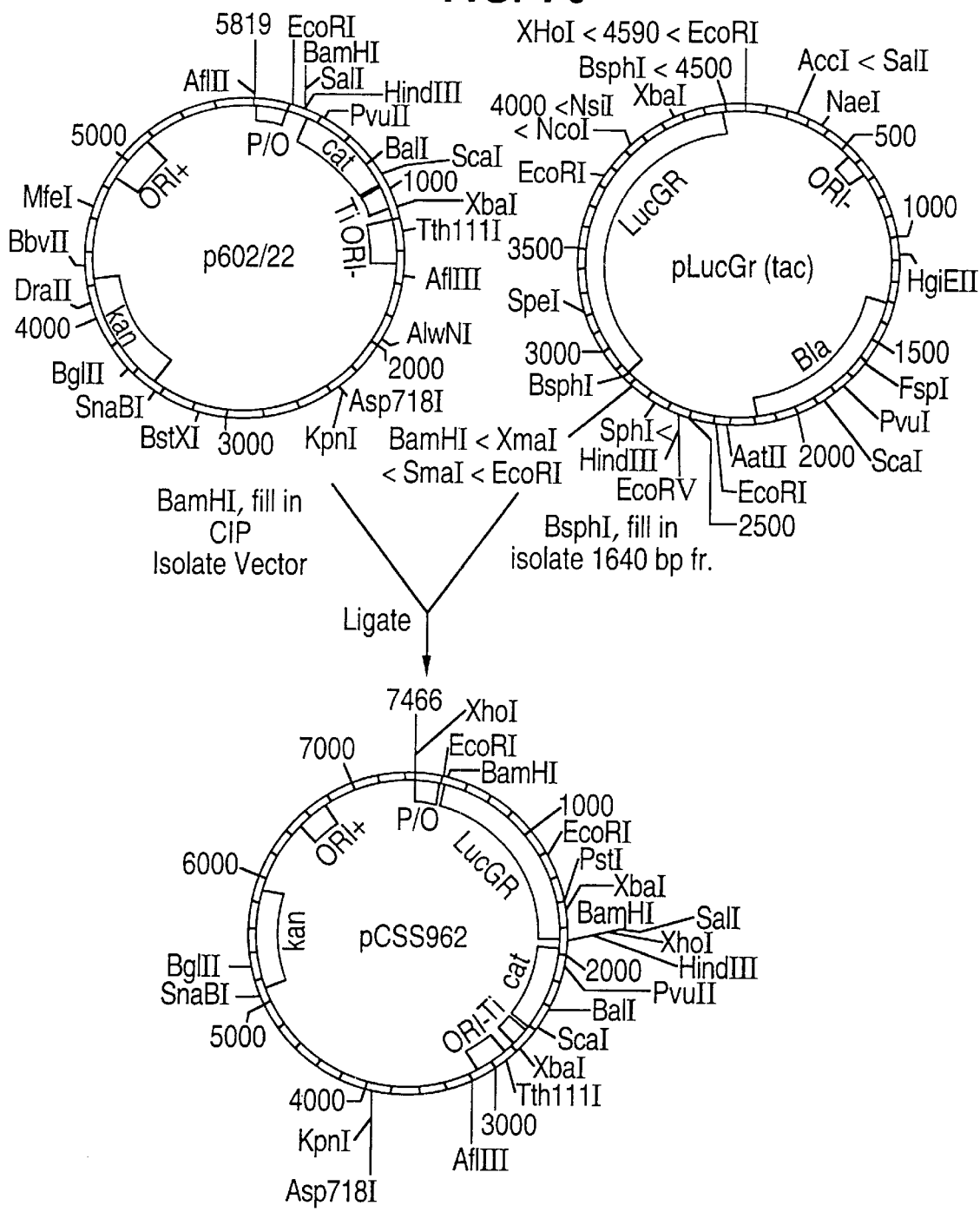
FIG. 7c shows construction of plasmid pCSS962.

Plasmid pCSS962 was constructed as follows: A shuttle vector p602/22, which can replicate both in E. coli and in B. subtilis (LeGrice et al., 1987, GENE, 55, 95–103) was cut with restriction enzyme BamHI, filled in with Klenow enzyme and treated with calf intestinal alkaline phosphatase (CIP). The plasmid pLucGR(tac) containing a green click beetle luciferase gene was digested with restriction enzyme BspHI, filled in with Klenow enzyme and separated on an agarose gel as described above. The gene and the vector were ligated together. The ligation mixture was transformed into E. coli MC1061 as described below and correct plasmid constructions were verified by analyzing the plasmid minipreparations with suitable restriction enzyme analysis. The correct plasmid was co-transformed with a helper plasmid pBL1 (LeGrice et al., 1987, GENE, 55, 95–103) into B. subtilis 1A40 strain as described below. The plasmid and its construction are shown in FIG. 7c. The symbols used are: P/O=Promoter/Operator; ori+=E. coli origin of replication; ori+=B. subtilis origin of replication; kan=gene encoding kanamycin acetyltransferase; cat=gene encoding chloramphenicol acetyltransferase; T1=transcriptional terminator.

The competence induction of E. coli strains: E. coli strains were made competent, i.e., able to take foreign DNA inside the cell as follows: E. coli were grown overnight in a volume of 5 ml in 2×TY medium and transferred to 100 ml of the same medium. After about two hours, the optical density, as measured at 600 nm, was 0.8. The cells were cooled in an ice bath and centrifuged at 4000×g for 5 min. The cell pellet was suspended in 50 ml of 50 mM $CaCl_2$ and centrifuged at 3000×g for 5 min at 0° C. The cells were suspended in 4 ml of 50 mM $CaCl_2$ containing glycerol 15%. These competent cells were divided in 1 ml aliquotes and they were frozen rapidly in liquid nitrogen and stored at −70° C. for later use.

The competence induction of B. subtilis: B. subtilis 1A40 was grown overnight in 5 ml of 2×TY at 37° C., spun down and suspended in 15 ml of Growth Medium 1 [(SMS=$(NH_4)_2SO_4$ 0.2%, $K_2HPO_4$ 1.4%, $KH_2PO_4$ 0.6%, Na-citrate 0.1%, $MgSO_4$ 0.02%), glucose 0.5%, casamino acids 0.05%, yeast extract 0.06%, $MgCl_2$ 1.5 mM] and grown until the optical density was 1.8 as measured at 600 nm. The culture was then transferred to 150 ml of Growth Medium 2 [(SMS, glucose 0.5%, casamino acids 0.01%, yeast extract 0.025%, $MgCl_2$ 5 mM, $Ca(NO_3)_2$ 2.5 mM] for 90 minutes at 37° C. After centrifugation at 8000 rpm for 5 minutes at room temperature, the pellet was suspended in 15 ml of the supernatant. Glycerol was added to 8% and cells were divided into 1 ml aliquotes and quickly frozen in liquid $N_2$ and stored at −70° C.

The Transformation of E. coli Strains with rec-DNA Plasmids

One to ten μl plasmid-DNA or ligation mixture was added to microcentrifuge tubes prechilled in an ice bath. To these, 250 μl of competent-cells and 26 μl of 10×TMC (100 mM TRIS-HCl, pH 7.4, 100 mM $MgCl_2$, 100 mM $CaCl_2$) were added and kept in an ice bath for 10 min with occasional careful mixing. The cells were heat shocked for two minutes at 42° C. and then one ml of 2×TY was added. The cells were kept thereafter at 30° C. for one hour and centrifuged for 3 min at 8000×g. The supernatant was discarded and cells were suspended in the leftover supernatant (about 100 μl). The cell suspension was spread on antibiotic selection plates and incubated at 30° C. overnight.

The transformation of B. subtilis with rec-DNA plasmids: One ml of frozen competent B. subtilis cells were quickly melted in a 37° C. waterbath and they were diluted in 10 ml of SMS Dilution Medium (SMS, glucose 0.5%, $MgCl_2$ 20 mM, EDTA 1 mM). One ml of diluted cells were mixed with 1 μg of pCSS962 and 1 pg of pBL1 and incubated at 37° C. for 30 minutes with shaking. Subsequently, cells were plated on 2×TY plates containing 10 μg/ml of kanamycin and erythromycin. Plates were incubated at 30° C. for 22 hours.

Example 1

The Change in Plasmid Copy-number when Cells are Treated with Nalidixic Acid

The plasmid pCSS123 described in the instant invention is a runaway-replication plasmid, in which a change in copy number can be obtained by shifting the temperature (FIG. 8). The effect of nalidixic acid, an agent known to inhibit DNA replication of cell DNA and especially of plasmid pCSS123 DNA, is shown in FIG. 8. FIG. 8 shows the amount and quality of plasmid-DNA extracted from heat-treated E. coli cells.

E. coli pCSS123/JM103 cells were cultivated in 20 ml of 2×TY at 30° C. in four Erlenmeyer bottles until the absorbance measured at 600 nm was 0.3. Nalidixic acid, a known inhibitor of DNA replication, was added to a final concentration of 0, 1, 10 and 100 µg/ml. Parallel samples of 1.5 ml from each bottle were immediately withdrawn to 15 ml tubes and kept at 30° C. for 20 min. The tubes were transferred to 42° C. for one hour and the bottles were left at 30° C. After one hour, both the tubes and the bottles were kept for an additional hour at 30° C. in a shaker. Total-DNA was extracted from 1.5 ml of culture.

Cells were centrifuged and the pellets were suspended in 500 µl 50 mM TRIS-HC1, pH 8.0, 50 mM EDTA. Cells were kept in an ice bath for 30 min and 50 µl of lysozyme (10 mg/ml) was added and kept in an ice bath for 45 min. One hundred µl of STEP solution (0.5% SDS, 50 mM TRIS-HC1, pH 7.5, 0.4 M EDTA) was added and kept at 50° C. for 60 min. After this, 600 µl of phenol was added and the tubes were gently mixed for 5 min and centrifuged 10 min at 12000×g. Two volumes of absolute ethanol and K-acetate, pH 6.0 to 0.3 M, were added to the supernatant to precipitate the DNA. After 30 min at −70° C. the tubes were centrifuged 10 min at 12000×g and the pellet was washed with 500 µl of 70% ethanol, centrifuged and the pellets were dried in a vacuum exiccator for 5 min. The dried pellet was dissolved in 50 µl of 50 mM TRIS-HC1, pH 7.5, 1 mM EDTA, 100 µg/ml RNAase A solution and kept at 65° C. for 20 min. A conventional agarose gel electrophoresis analysis was made for the extracted DNA's. As shown in FIG. 8, the DNA content did not change in the samples which were not heat-treated. In contrast, the DNA content increased several fold in samples which were heat-treated and not treated with nalidixic acid. DNA content was unaffected by the presence of 1 µg or higher nalidixic acid whether the cells were heat-treated or not.

Example 2

Figure 9A:
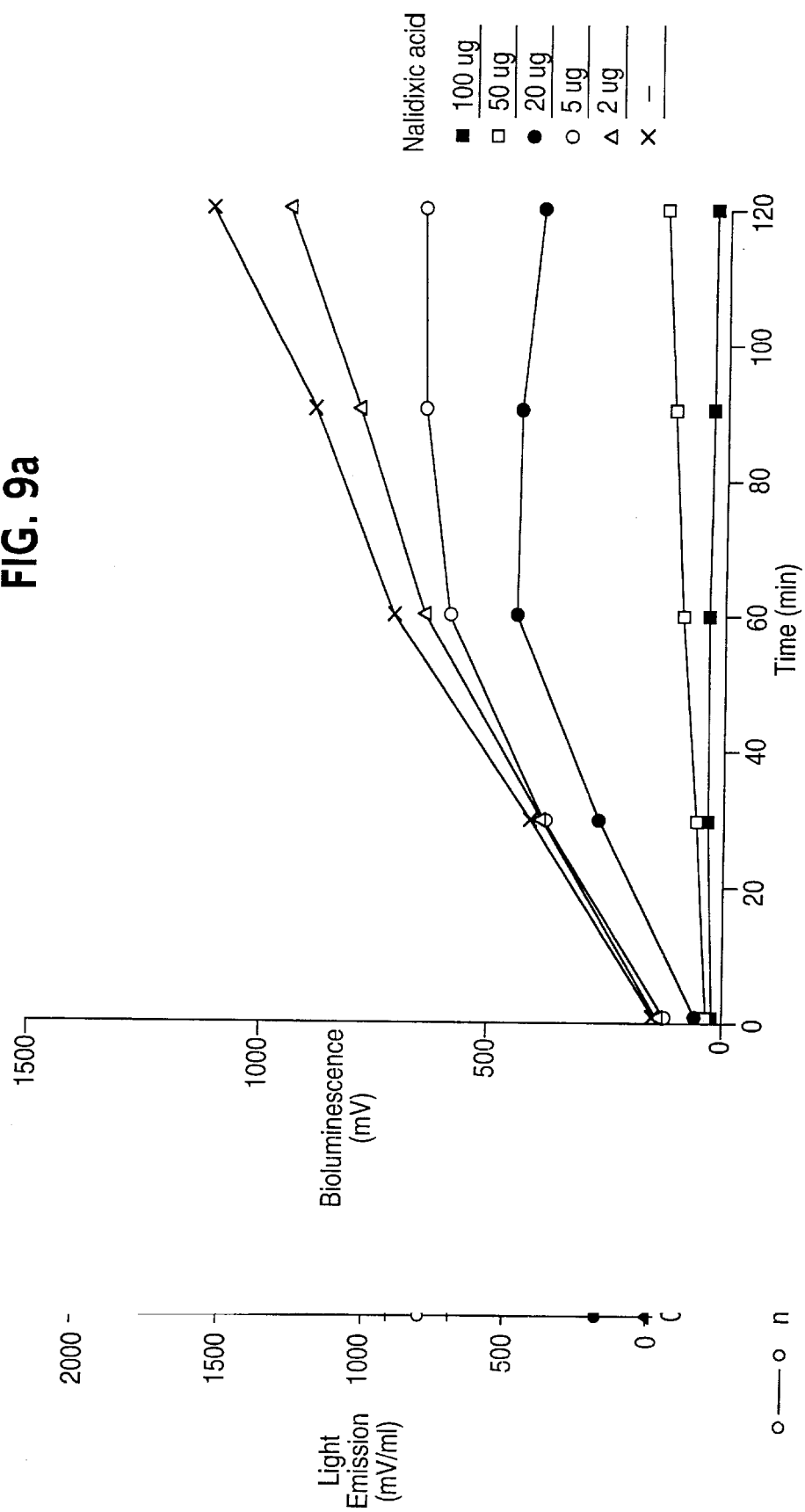
FIG. 9a shows the detection of nalidixic acid using *E. coli* cells cloned with pCSS123.

Determination of Toxic Substances as Measured by the Help of Light Production by Cells Containing Plasmid Whose Copy Number Can be Changed E. coli pCSS123/JM103 cells grown overnight were diluted 1:1000. Diluted cells in 2×TY were taken (0.5 ml) and various amounts of antibiotics or other toxic substances were added. These solutions were incubated 20 min at 30° C. After this the samples were transferred to 42° C. for one hour. Each tube was thereafter incubated at 30° C. in a waterbath and IPTG was added to 1 mM and n-decanal to 0.01%. The tubes were transferred to an automated light-gathering device, i.e., luminometer 1251 (LKB-Wallac, Turku, Finland) whose measuring chamber had been equilibrated to 30° C. Measurement of light emission by the cells was done with the auto-mode program so that each tube was automatically measured every two minutes. Data were collected in the memory of the computer for later analyses. FIG. 9a shows the detection of nalidixic acid using E. coli cells cloned with pCSS123 As shown in FIG. 9a, 2 µg of nalidixic acid can be detected very quickly. FIG. 9b shows the detection of chloramphenicol using E. coli cells cloned with pCSS123. For clarity reasons only two concentrations of chloramphenicol were compared to the untreated control.

FIG. 9c shows the detection of heavy metal cadmium using E. coli cells cloned with pCSS123.

Freeze-dried E. coli pCSS123/BW322 were reconstituted with 1.0 ml of 2×TY and 45 µl of this was diluted 1:10 with 2×TY. Five µl of trimethoprim dilutions were added and kept at room temperature for 25 minutes. Cells were heat induced at 42° C. for 25 minutes and equilibrated to 30° C. in a water bath for 10 minutes. n-decanal was added to 0.001% and light production was measured using a LKB-Wallac 1250 manual luminometer. Same concentrations of trimethoprim together with reconstituted, freeze-dried cells which were not heat-treated acted as controls. FIG. 9d shows the detection of trimethoprim using E. coli cells cloned with pCSS123. As shown in FIG. 9d, the sensitivity of the assay is very high. FIG. 9e shows the detection of oflaxacin using the same approach as in FIG. 9d.

One hundred µl of reconstituted E. coli pCSS123/BW322 were plated onto a Petri dish. The effect of UV light (254 nm) was tested by varying the time of exposure. Following exposure, the samples were transferred to 42° C. for 45 min and n-decanal to 0.01% was added. Light output was determined as described above. FIG. 9f shows light output for E. coli cells cloned with pCSS123 and treated with UV light.

Figure 9G:
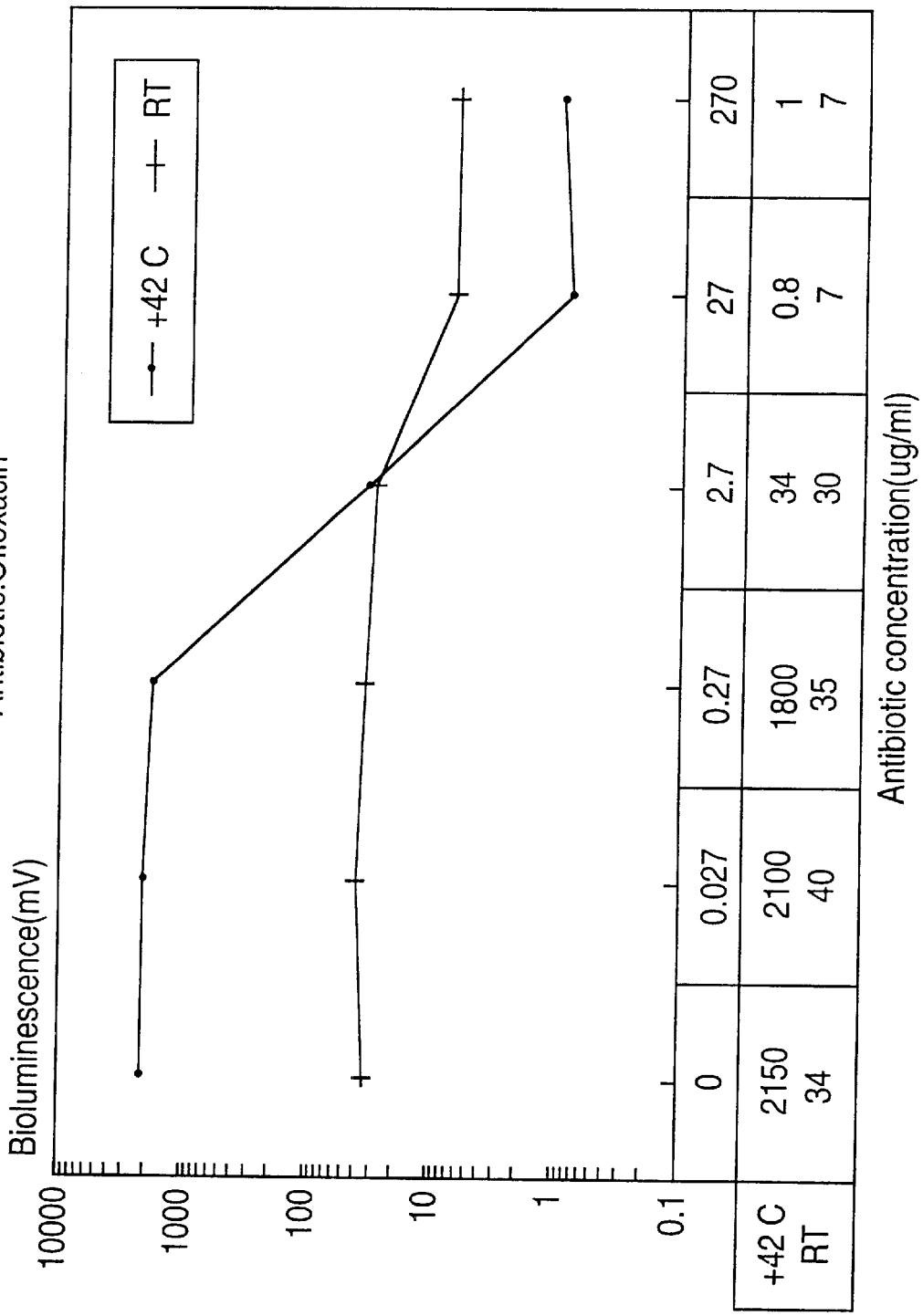
FIG. 9g shows the detection of oflaxacin using *E. coli* cells cloned with pCSS302.
Figure 9H:
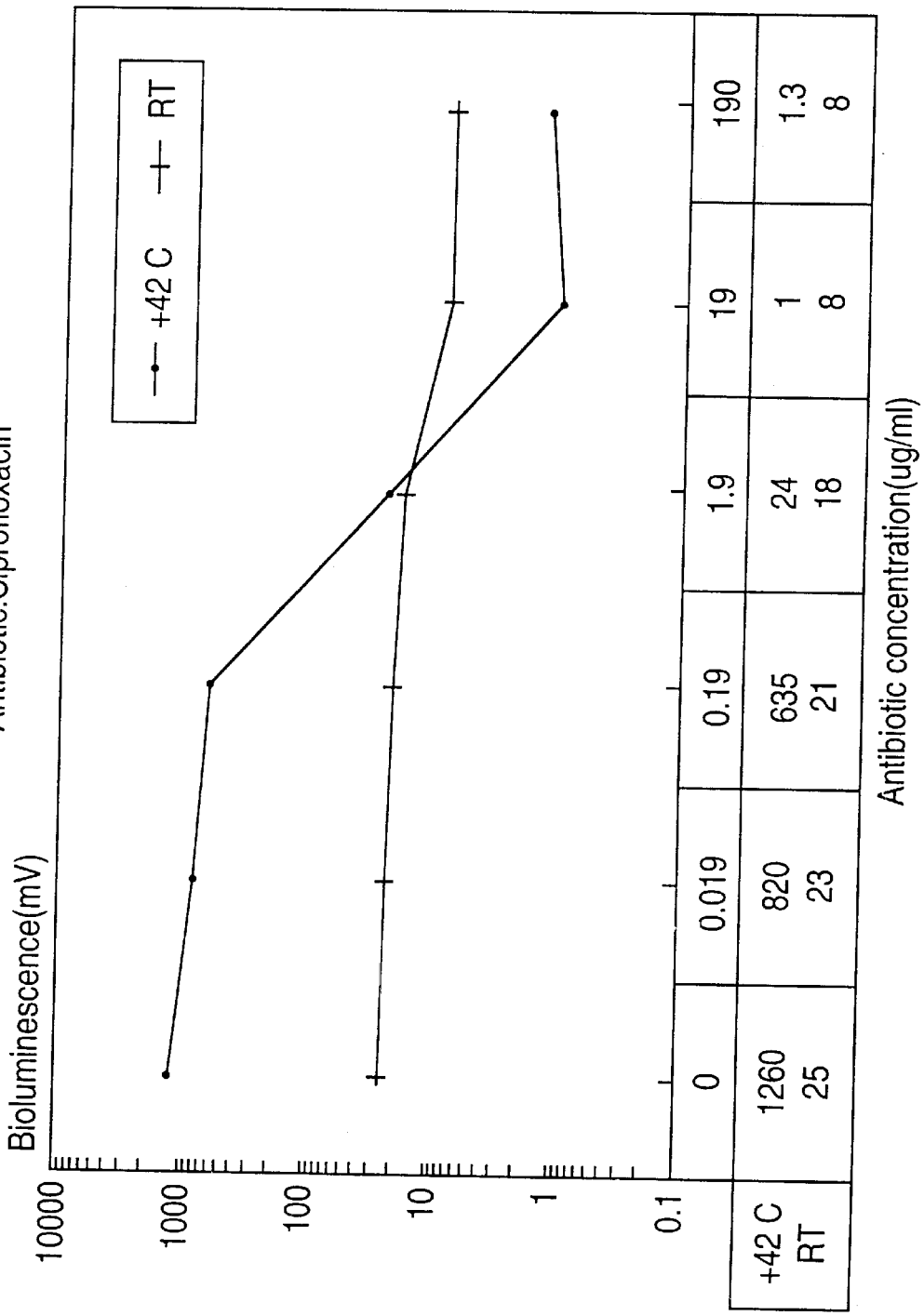
FIG. 9h shows the detection of citroflaxicin using *E. coli* cells cloned with pCSS302.

E. coli pCSS302/BW322 cells grown overnight were diluted in 2×TY. Ninety µl of the diluted cells were taken and antibiotics (laxacin or citrofloxacin) were added. The solutions were incubated for 20 min at RT. After this, the samples were transferred to 42° C. for 45 min. The cells were measured for light production by adding 100 µl of solution containing 1 MM D-luciferin and 1 mM ATP in 0.1M Na-citrate buffer, pH 5.0. FIG. 9g the detection of oflaxacin using E. coli cells cloned with pCSS302. FIG. 9h shows the detection of citrofloxacin using E. coli cells cloned with pCSS302.

E. coli pCSS305/BW322 cells were used to test a system where no substrate addition was needed to produce light from cells. To 90 µl of the cells in 2×TY, 10 µl of the antibiotics was added. Different concentrations of oflaxacin (FIG. 9j) and citrofloxacin (FIG. 9i) were added and the tubes were kept at RT for 25 min. After this the induction was done by shifting the tubes to 42° C. for 45 min. The tubes were loaded in the luminometer for light production measurement. FIG. 9j shows the detection of oflaxacin using E. coli cells cloned with pCSS305. FIG. 9i shows the detection of citrofloxacin using E. coli cells cloned with pCSS305.

Example 3

Figure 11A:
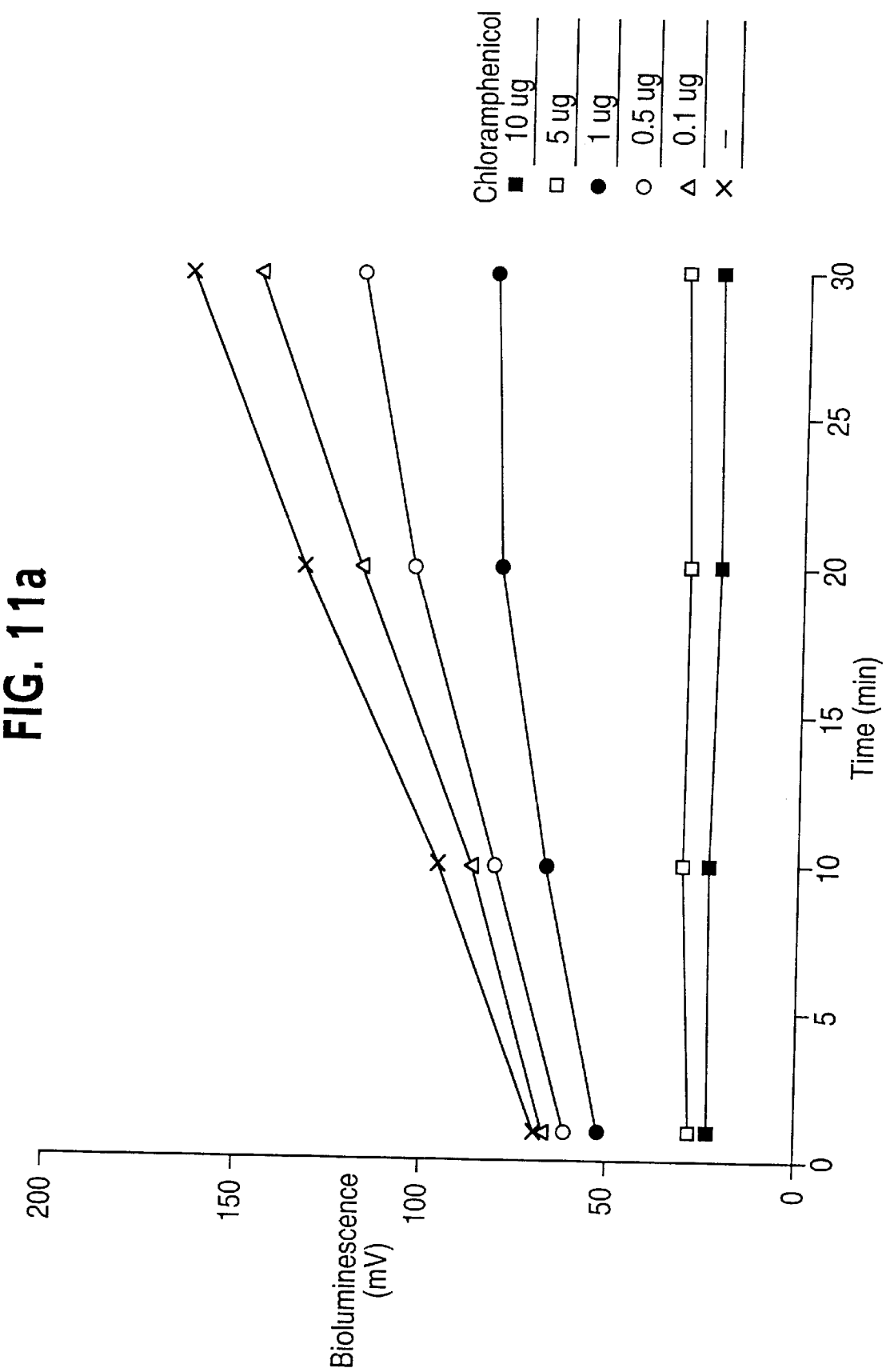
FIG. 11a shows the kinetics of light production for *E. coli* K-12 HI trp(c1857) cells cloned with pCSS112 and treated with chloramphenicol.
Figure 12:
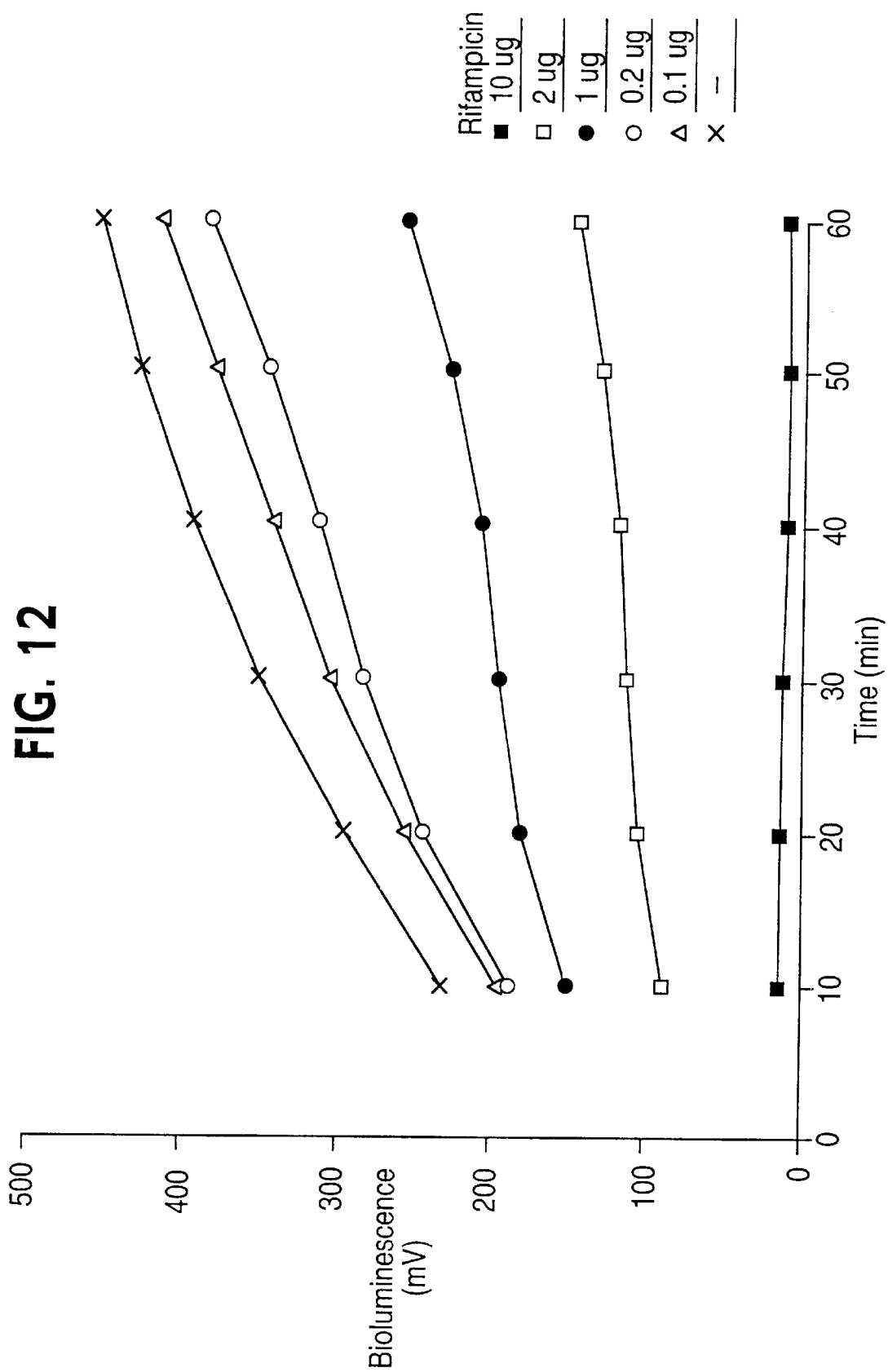
FIG. 12 shows the detection of rifamicin

The Detection of Antibiotics with a Method Where Control of Plasmid Replication is not Possible A comparison is made between plasmids where the expression of bacterial luciferase genes are controlled by either lac (slow) or $P_L$ promoter (fast) promoters. E. coli clone pCSS112/K-12 HI trp(c1857) was grown overnight in 2×TY medium containing ampicillin 100 µg/ml. After this a suitable dilution was made in HBSS-buffer or in milk and 500 µl of this was added to 3 ml luminometer tubes. The tubes were equilibrated to 30° C. and different amounts of various toxic substances were added to tubes. Tubes were kept at 30° C. for 20 min, after which the temperature was shifted to 42° C. for 10 minutes. Thereafter the tubes were removed to luminometer chamber which had been equilibrated to 30° C. for automated measurement. As a comparison, an E. coli JM103 clone containing plasmid pCSS108 was used as a control. The control cells were treated similarly but without the heat-shock step. Messenger RNA and protein synthesis were induced in the control cells by adding IPTG to 1 mM. FIG. 10 shows a comparison of the detection of toxic substances in *E. coli* cells where protein synthesis is directed by the $P_L$ promoter or the lac promoter. As shown in FIG. 10, when $P_L$ promoter directs protein synthesis it is possible to detect toxic substance in much lower concentrations than using the slower and weaker lac promoter. In case of chloramphenicol, the kinetics of light production have been shown in FIG. 11*a* when plasmid pCSS112 in *E. coli* K-12 HI trp(c1857) strain is used. FIG. 12 shows that differences in the measured activity (light production) are seen from the start of measurement even with concentrations as low as 0.1 μg/ml in the measuring cuvette.

The detection of antibiotics belonging to the penicillin family is of utmost importance since these antibiotics are very widely used and quick methods do not exist to detect their presence. FIG. 11*b* shows the detection of ampicillin, oxytetracyclin, and streptomycin using *B. subtilis* 1A40 cells cloned with luciferase gene from a click beetle. The plasmid used is shown in FIG. 7*c*. Using this construction, the production of luciferase can be turned on in *B. subtilis* by simple addition of IPTG, which binds to the lac repressor coded by the helper plasmid pBL1 present in the same cell. After IPTG binds to the repressor, the repressor cannot bind to the DNA region between phage T5 promoter and the luciferase gene thus allowing the expression of luciferase. Cells containing both plasmids were cultured overnight in 2×TY containing erythromycin (10 μg/ml, to keep pBL1 in the cell) and kanamycin (10 μg/ml, to keep pCSS952 in the cell). A suitable dilution was made and different amounts of antibiotic were added to the cells. After an incubation period of 2 hours at 30° C., the tubes were measured for light emission after addition of 1 mM D-luciferin substrate in 0.1 M Na-citrate. As shown in FIG. 11*b* a low amount of 0.1 ug/ml ampicillin and even lower amounts of oxytetracyclin and streptomycin can be detected.

Example 4

Detection of Toxic Substances Using a Method Where *E. coli* Contains Constant Copy-number rec-DNA Plasmid and in Which Promoter of Phage Lambda Controls the Biosynthesis of Bacterial Luciferase and Click Beetle Luciferase The following examples show detection of substances affecting other biosynthetic routes and metabolism of cells. The tests have been performed in the same way as those described in previous examples. The goal has been to develop an extremely rapid method, which is also very sensitive. Plasmid pCSS112 cloned in the *E. coli* K-12 strain was used throughout the following examples.

The following figures show the effect of each tested substance as measured by light production. As in earlier measurements, the presence of inhibiting factors is seen as lowered light production compared to cases where the factor has not been present. Shown in FIG. 12 is the detection of an antibiotic, rifampicin, which is a known inhibitor of transcription, i.e., formation of messenger RNA.

Figure 14A:
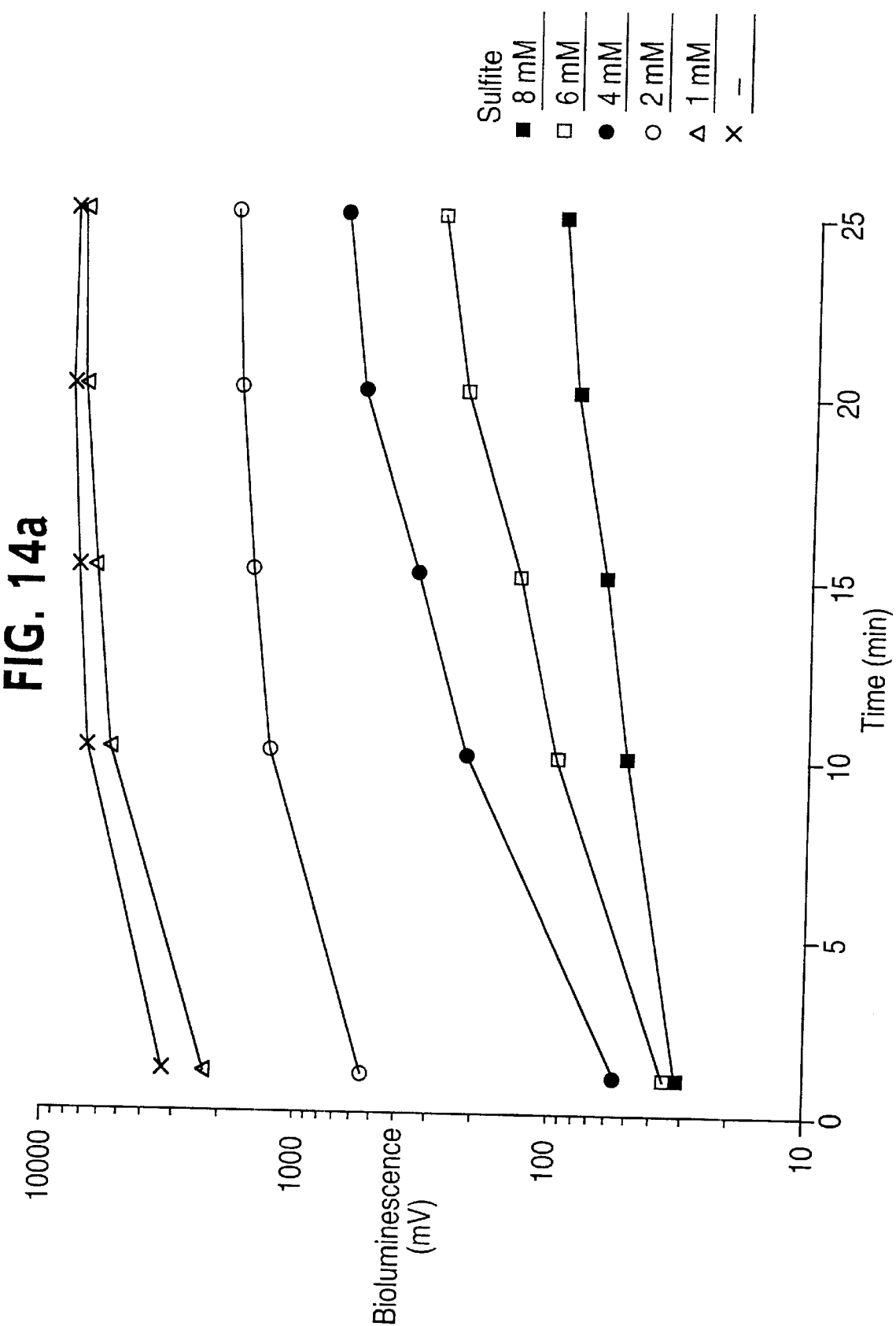
FIG. 14a shows the detection of sulphite.
Figure 14B:
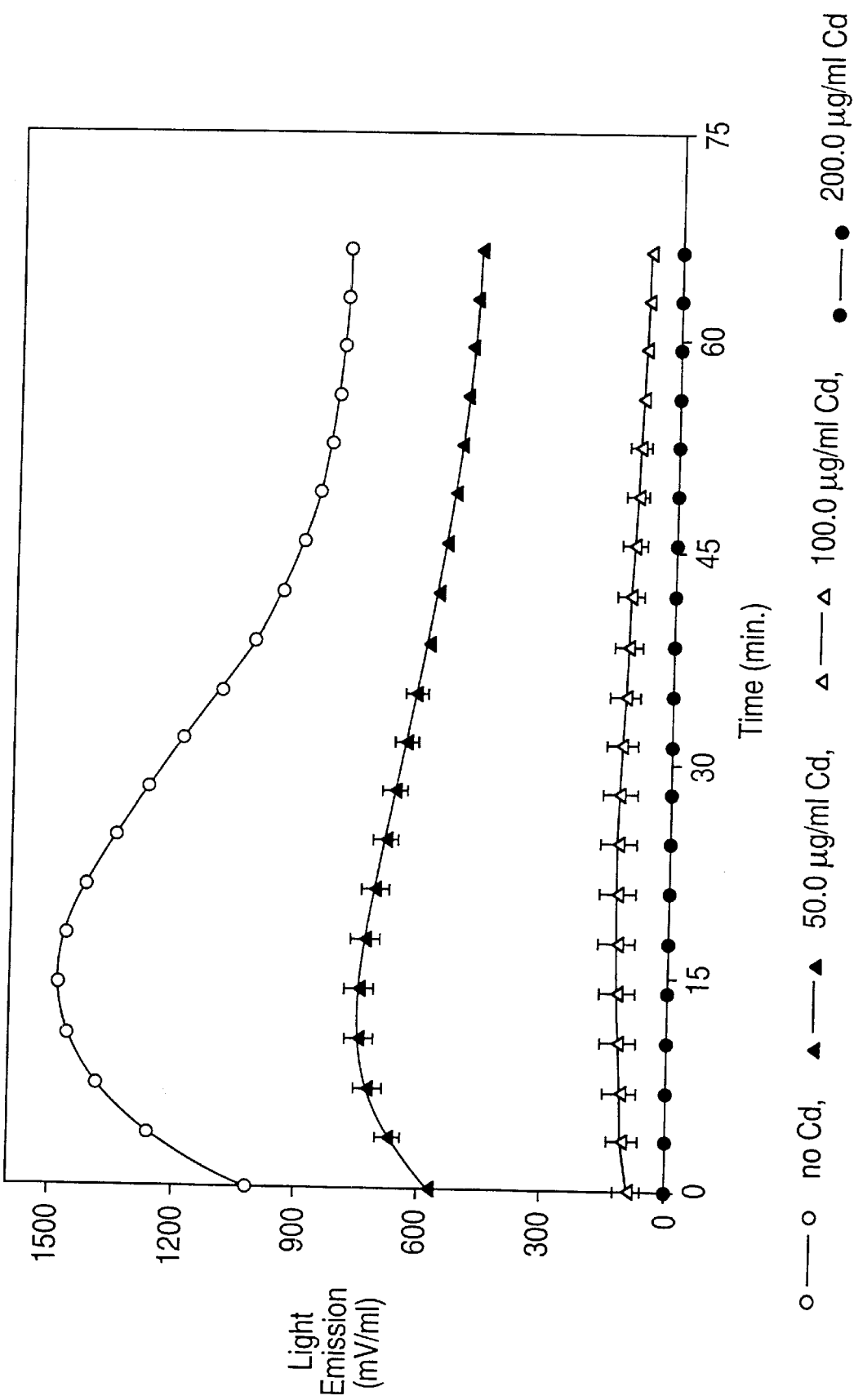
FIG. 14b shows the detection of cadmium, a heavy metal.

Oxytetracycline is an antibiotic which binds to the 30S ribosomal subunit. FIG. 13 shows the effect of oxytetracycline on light output in *E. coli* cells cloned with pCSS112. Amounts as low as one μg can be seen very rapidly with the method described in this invention. The effect of oxytetracycline is strong and easily detected. The effect of sulphite which is a known inhibitor of metabolism and used in food processing is shown in FIG. 14*a*. The effect of heavy metal cadmium, which is also a known inhibitor of metabolism and contaminates soil and water, is shown in FIG. 14*b*. These results show that the test system described in this invention is also applicable to the quick determination of metabolic inhibitors. In addition, it shows that the method can detect the presence of agents other than antibiotics.

Figure 15:
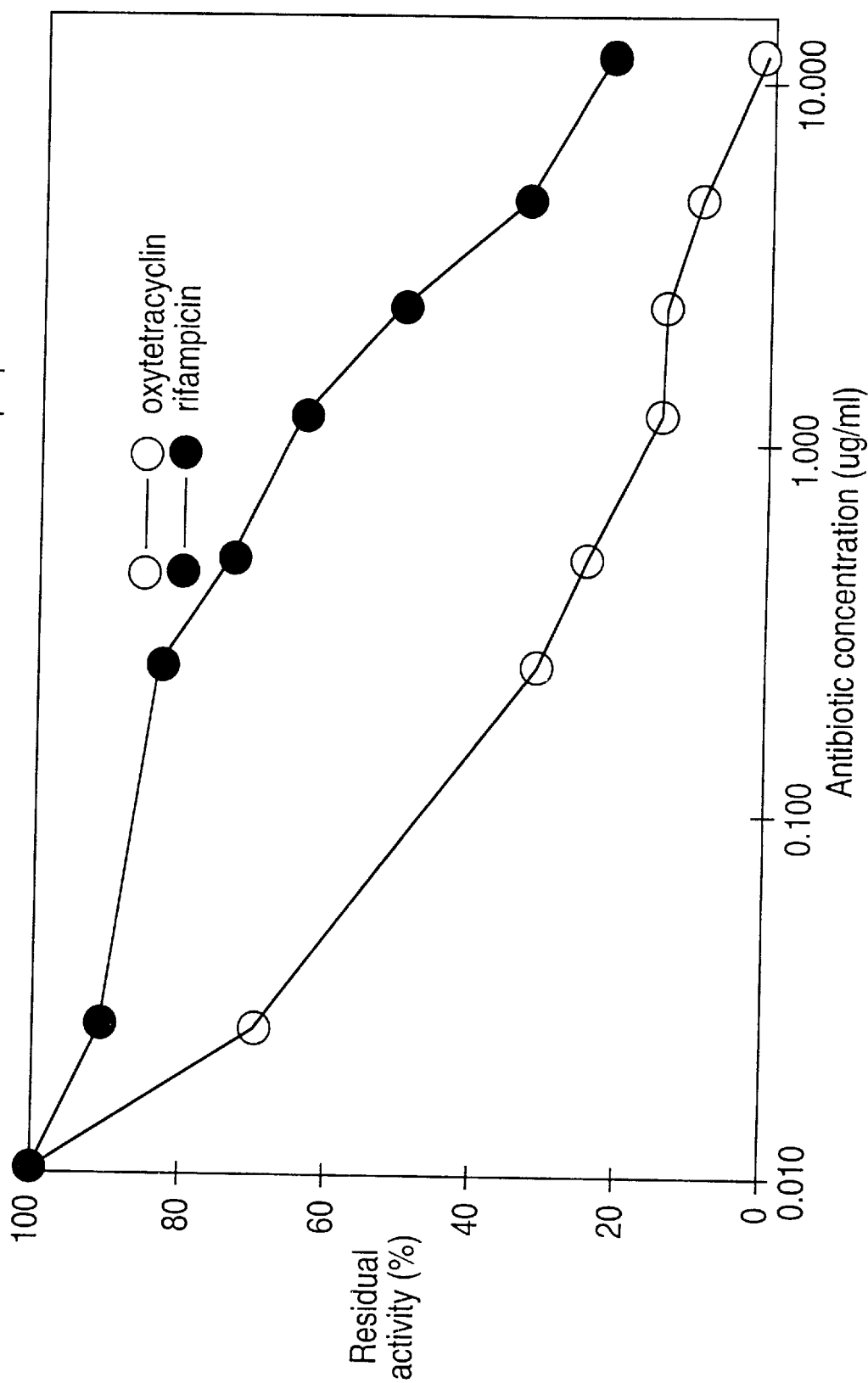
FIG. 15 shows the detection of rifampicin or oxytetracyclin using click beetle luciferase.

In addition to bacterial luciferase, other luciferases can be used without losing the sensitivity or performance of the test. FIG. 15 shows light output of *E. coli* cloned with pCSS301 and treated with oxytetracycline or rifampicin The plasmid (pCSS301) used in this test contains the click beetle luciferase gene as described in FIG. 7*b*. The test was done essentially as that described for bacterial luciferase except that after the cells were incubated with or without toxic substances, the cells were measured for light production after 15 minutes at 30° C. by adding 100 μl of solution containing 1 mM D-luciferin, 1 mM ATP in 0.1 M Na-citrate buffer, pH 5.0. Thereafter the light production was measured using a manual luminometer 1250 (LKB-Wallac, Turku, Finland). As can be seen from FIG. 15, the sensitivity of the method to detect either oxytetracycline or rifampicin is extremely high and comparable to the detection made with bacterial luciferase.

Example 5

The Determination of a Toxic Substance Using a Method Where $P_{L-}$ promoter of Phage Lambda Activates the Biosynthetic Machinery to Produce β-galactosidase In the previous examples, measurements were based on light produced from luciferase genes. However, any protein or peptide can be used provided a method for detecting the protein or peptide exists. In this example, β-galactosidase is used in place of luciferase. The plasmid pPLcAT14 used has been described elsewhere (Stanssens, P., Remaut, E. & Fiers, W., 1985, GENE, 36, 211–223).

Figure 16:
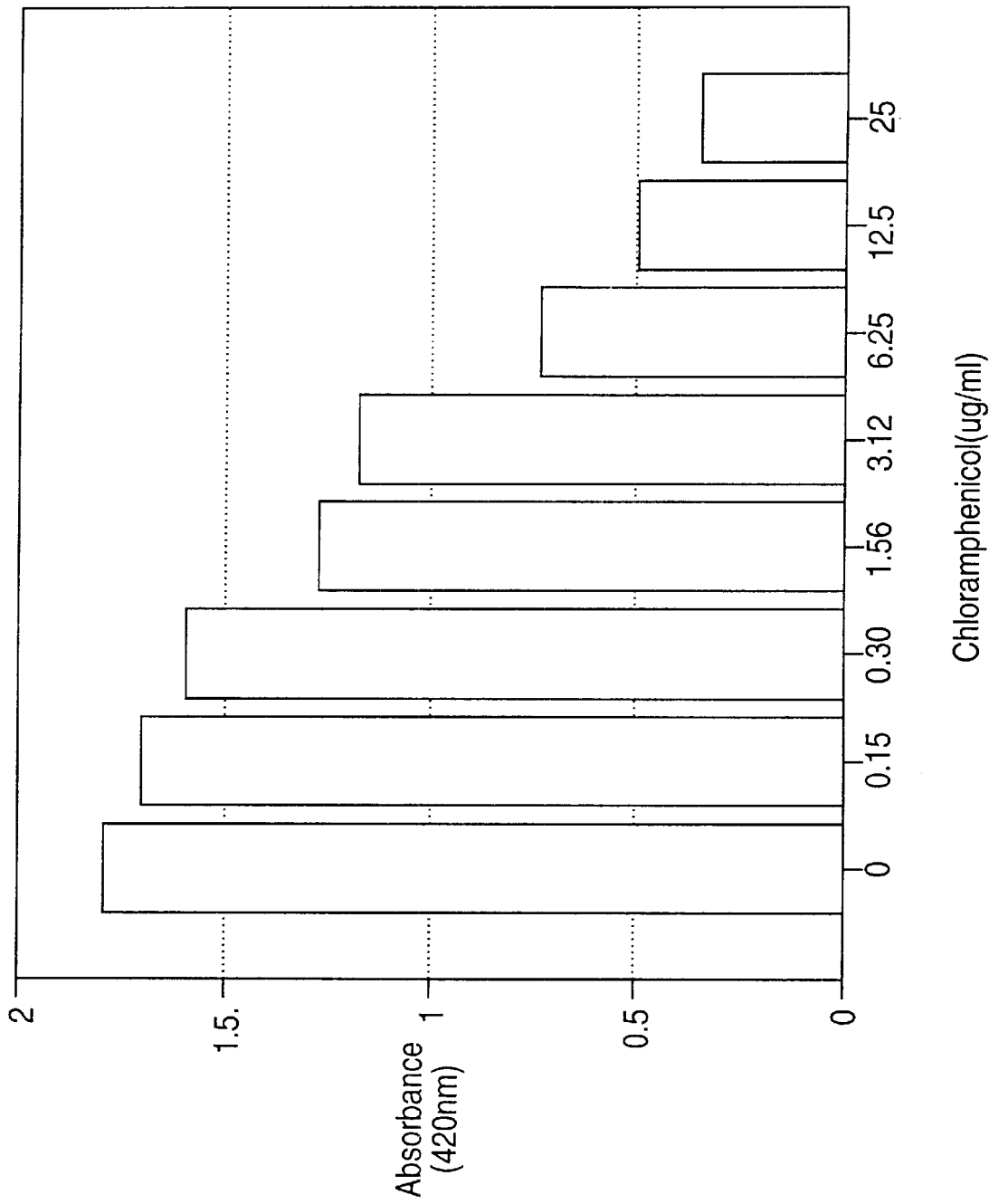
FIG. 16 shows the detection of chloramphenicol using β-galactosidase.

*E. coli* clones pPLcAT14/K-12 HI trp were grown overnight in 2×TY medium which was supplemented with ampicillin 100 μg/ml. After this a suitable dilution was made from bacteria in HBSS buffer and 80 μl of this was added to glass tubes. Different concentrations of chloramphenicol were added and tubes were kept at room temperature for 15 minutes. After incubation, activation of the $P_L$ promoter was induced by shifting the tubes to 42° C. for 30 minutes. As a consequence the biosynthesis machinery is activated to produce β-galactosidase encoded by the β-galactosidase gene cloned under $P_L$ promoter in plasmid pPLcAT14. After induction, toluene was added to 10%. Toluene makes the cells porous to a chemical, ONPG. Following reaction of ONPG with β-galactosidase, a yellow color forms. The yellow color can be measured with a spectrophotometer at 420 nm. FIG. 16 shows the amount of β-galactosidase produced in *E. coli* cloned with pPLcAT14, induced with IPTG in the presence of chloramphenicol.

Example 6

Determination of Organic Content in a Solution Using a Method Where $P_L$ promoter of Phage Lambda Activates the Biosynthetic Machinery to Produce Luciferase

Figure 17:
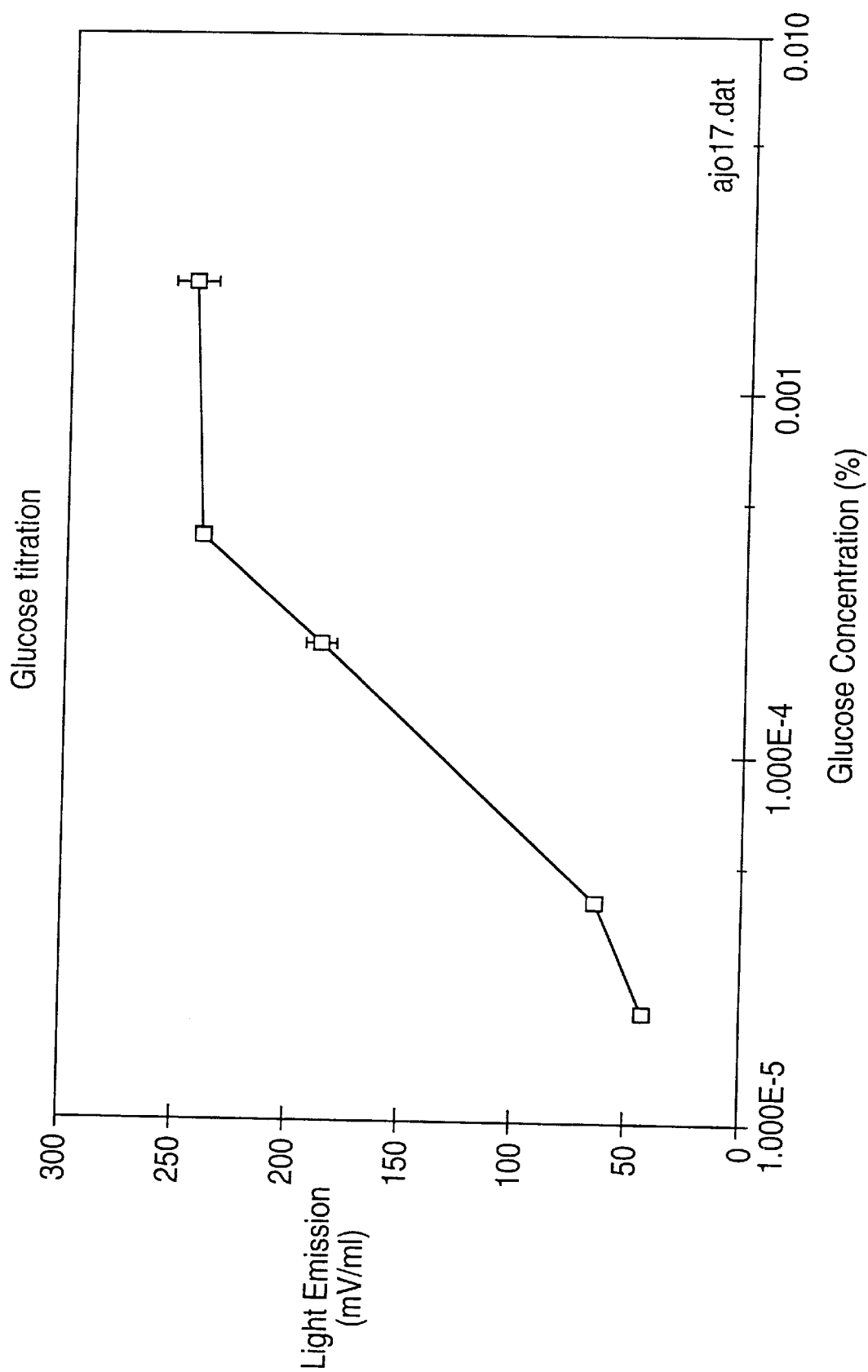
FIG. 17 shows the detection of glucose.

*E. coli* pCSS112/K-12 HI trp cells were cultivated overnight in 2×TY containing ampicillin (100 μg/ml). Cells were spun down and washed twice with a HBSS medium (Korpela & Karp, 1988, Biotech. Lett., 10, 383–388) omitting glucose and gelatine but supplemented with tryptophane 0.02%. The cells were shaken in this medium for 4 hours, spun down and suspended in HBSS buffer containing either 0.1% glucose or 0.1% $(NH_4)_2SO_4$ depending on whether carbon sources or nitrogen sources were evaluated, respectively. A suitable dilution was made from treated cells in minimal salts and various amounts of either carbon or nitrogen sources were added. The cells were incubated 10 minutes at 30° C. A heat treatment of 10 minutes at 42° C. was given to the cells to start the protein synthesis. The cells were then incubated 10 minutes at 30° C. and then the tubes were loaded in the automated luminometer for light production measurements after addition of n-decanal to 0.001%. FIG. 17 shows the detection of glucose.

TABLE 1

Biochemical targets for drug action:

| Cell walls | Inhibitors of protein synthesis | Inhibitors of nucleic acid synthesis |
|---|---|---|
| beta-lactams acid | chloramphenicol | nalidixic |
| cephalosporins | tetracyclines | novobiocin |
| bacitracin | aminoglycosides | rifamycins |
| vancomycin | macrolides | |
| | phleomycin | |
| polymyxins | erythromycin | |
| | mithramycin | |
| gramicidins | lincomycin | |
| | actinomycin | |
| valinomycin | puromycin | quinolones |

What is claimed is:

1. A method for determining the presence or amount of at least one inhibitory factor in the sample to be tested, wherein the inhibitory factor inhibits one or more of DNA synthesis, transcription of DNA, translation of RNA, cell wall synthesis, cell membrane function or metabolic functions which participate in or influence these processes, said method comprising:
   a) incubating a sample to be tested with a population of transformed cells for a period sufficient to allow an inhibitory factor, if present in the sample, to affect said cells, said cells being transformed with a recombinant DNA plasmid, and replication of said plasmid being inducible by an exogenous stimulus independent of replication of the cells and further wherein said cells are sensitive to inhibition by the inhibitory factor;
   b) then applying said exogenous stimulus to said cells in an amount sufficient to induce replication of said plasmid in the absence of the inhibitory factor; and
   c) determining the amount of DNA produced by said population of cells, the amount of the inhibitory factor in said sample being correlated with a reduction in the amount of DNA produced compared to the amount of DNA produced by a like cell population by application of a like amount of exogenous stimulus in the absence of said sample.

2. The method of claim 1, wherein said exogenous stimulus is change of temperature.

3. The method of claim 1, wherein said exogenous stimulus is a chemical inducer.

4. The method of claim 1, wherein said recombinant plasmid contains DNA encoding an expressible enzyme and said step of determining the amount of DNA comprises measuring the activity of said enzyme.

5. A method according to claim 1, wherein the recombinant DNA plasmid contains a DNA sequence which encodes at least one selected protein or a part of said selected protein that is essential for biological activity of said protein and wherein the recombinant DNA plasmid comprises one or more DNA sequences which make the cell resistant to an antibiotic, heavy metal or toxin.

6. A method according to claim 5, wherein the DNA sequence encoding the protein is subject to a regulatable promoter, which is controlled by positive or negative feedback and is regulatable in said cells and is activated simultaneously or at a desired moment subsequent to induction of plasmid replication.

7. A method according to claim 6, wherein the factor is selected from the group consisting of aflatoxins, heavy metals, ethidium bromide, nalidixic acid, trimethoprim, fluoroquinolones, aminoglycocides, penicillines, cephalosporines, rifampicin, chloramphenicol, tetracyclines, and sulphonamides, and wherein the cell used is sensitive to said factor.

8. A method according to claim 7, wherein the cells are *Escherichia coli* and replication of the recombinant DNA plasmid contained in the cells can be accurately regulated by means of a strong promoter selected from the group consisting of lambda $P_L$ and $P_R$ promoters, lac, trp, and hybrid tac promoters.

9. A method according to claim 8, characterized in that the recombinant DNA plasmid is pCSS 123, pCSS302 or pCSS305, deposited under DSM number 5119, 7503 or 7504, respectively.

10. A method for determining the presence or amount of at least one inhibitory factor in the sample to be tested, wherein the inhibitory factor inhibits one of more of DNA synthesis, transcription of DNA, translation of RNA, cell wall synthesis, cell membrane function or metabolic functions which participate in or influence these processes, said method comprising:
   a) incubating a sample to be tested with a population of transformed cells for a period sufficient to allow the inhibitory factor, if present in the sample, to affect said cells, said cells being transformed with a high copy number recombinant DNA plasmid containing a sequence encoding a marker protein which is detectable when expressed, said sequence being coupled to a regulatable promoter such that expression of said marker protein is inducible by an exogenous stimulus;
   b) then applying said exogenous stimulus to said population of cells in an amount sufficient to induce expression of said marker protein in the absence of the inhibitory factor; and
   c) determining the amount of said marker protein expressed by said population of cells, the amount of the inhibitory factor in the sample being correlated with a reduction in the amount of said marker protein produced compared to the amount of said marker protein produced by a like cell population by application of a like amount of exogenous stimulus in the absence of the sample.

11. The method of claim 10, wherein said marker protein is luciferase.

12. A method according to claims 1 or 10, wherein the cell is a gram negative or gram positive bacteria belonging to the group Enterobacteriaceae or the group Bacillus.

13. A method according to claims 1 or 10, wherein the recombinant DNA plasmid comprises one or more DNA sequences, which make the cell resistant to an antibiotic, heavy metal, or toxin.

14. A method according to claims 1 or 10, wherein the sample to be tested is an aerosol.

15. A method according to claims 1 or 10, wherein the population of cells is lyophilized and is rehydrated before the step of incubating by a suitable liquid or cultivation medium.

16. A method according to claims 1 or 10, wherein the factor is selected from the group consisting of mutagens, antibiotics, heavy metals and toxins.

17. A method according to claim 16, wherein said cells are *Bacillus subtilis*.

18. A method according to claim 16, wherein said cells are *Escherichia coli*.

19. A method according to claim 17, wherein the marker protein is subject to a regulatable strong promoter selected from the group consisting of $\phi$ 105, phage T5 promoter controlled by lac operator and saccharose regulatable promoter, and the marker protein is selected from the group consisting of alpha-amylase, alkaline phosphatase, β-galactosidase, luciferase, peroxidase, T4 lysozyme, β-glucuronidase, oxidoreductase and pyrophosphatase.

20. A method according to claim 18, wherein the recombinant DNA plasmid contains a DNA sequence that encodes a marker protein and the expression of said protein is controllable by means of a regulatable promoter, selected from the group consisting of lac, trp, lambda $P_R$ and $P_L$, and tac promoters.

21. A method according to claim 20, wherein the protein is selected from the group consisting of luciferase, β-galactosidase, alkaline phosphatase, peroxidase, T4 lysozyme, β-glucuronidase, oxidoreductase and pyrophosphatase.

22. A method according to claims 19 or 21, wherein the recombinant DNA plasmid encodes a luciferase enzyme.

23. A method according to claim 22, wherein the recombinant DNA plasmid is plasmid pCSS112, pCSS301 or pCSS962.

24. A method according to claim 22, wherein an aldehyde is used to determine the amount of expressed luciferase in said cells.

25. A method according to claims 1 or 10, wherein the sample to be tested is milk, serum or water.

26. The method of claim 4, wherein said enzyme is luciferase.

27. A method for determining the presence of at least one inhibitory factor selected from the group consisting of ampicillin, chloramphenicol, oxytetracycline, streptomycin, erythromycin, ofloxacin, ciprofloxacin, actinomycin and trimethoprim in a sample of a biological fluid selected from the group consisting of blood, plasma, serum, urine, semen and milk, said method comprising:

a) obtaining a population of cells transformed with a high copy number recombinant DNA plasmid containing a sequence encoding luciferase, wherein said sequence is coupled to a regulatable promoter such that expression of said sequence is inducible by application of a chemical inducer to cells containing said plasmid;

b) incubating said sample with said cell population in a medium suitable for growth of said cells for a period sufficient to allow said inhibitory factor if present to affect said cells;

c) then applying said chemical inducer to said cells in an amount which in the absence of said inhibitory factor is sufficient to induce expression of said sequence; and d) determining the amount of luciferase expressed by said cell population, the amount of said inhibitory factor in said sample being correlated with the reduction in the amount of luciferase produced relative to the amount of luciferase produced by a like cell population by application of a like amount of said chemical inducer in the absence of said sample.

28. A method according to claims 1 or 10 wherein the sample to be tested is a body fluid of an animal, soil, water or milk.

* * * * *